US012364745B2

(12) United States Patent
Janssen et al.

(10) Patent No.: US 12,364,745 B2
(45) Date of Patent: Jul. 22, 2025

(54) IMMUNOGENICITY OF A CPG-ADJUVANTED RECOMBINANT PLAGUE VACCINE

(71) Applicants: Dynavax Technologies Corporation, Emeryville, CA (US); The Government of the United States, as Represented by the Secretary of the Army, Fort Detrick, MD (US)

(72) Inventors: Robert S. Janssen, Palm Springs, CA (US); David Novack, Oakland, CA (US); Wai Kwan Chung, Hagerstown, MD (US); Andrew M. Glenn, Germantown, MD (US); Lucy A. Ward, Silver Spring, MD (US)

(73) Assignees: Dynavax Technologies Corporation, Emeryville, CA (US); The Government of the United States, as Represented by the Secretary of the Army, Fort Detrick (MD)

( * ) Notice: Subject to any disclaimer, the term of this patent is extended or adjusted under 35 U.S.C. 154(b) by 0 days.

(21) Appl. No.: 18/344,780

(22) Filed: Jun. 29, 2023

(65) Prior Publication Data

US 2024/0165215 A1    May 23, 2024

Related U.S. Application Data

(60) Provisional application No. 63/357,542, filed on Jun. 30, 2022.

(51) Int. Cl.
*A61K 39/02* (2006.01)
*A61K 39/39* (2006.01)
*A61P 31/04* (2006.01)
*A61K 39/00* (2006.01)

(52) U.S. Cl.
CPC .......... *A61K 39/0291* (2013.01); *A61K 39/39* (2013.01); *A61P 31/04* (2018.01); *A61K 2039/545* (2013.01); *A61K 2039/55505* (2013.01); *A61K 2039/55561* (2013.01)

(58) Field of Classification Search
CPC ................ A61K 39/0291; A61K 39/39; A61K 2039/545; A61K 2039/55561; A61K 2039/575; A61P 31/04; Y02A 50/30
See application file for complete search history.

(56) References Cited

U.S. PATENT DOCUMENTS

| | | | |
|---|---|---|---|
| 6,589,940 B1 | 7/2003 | Raz et al. | |
| 7,718,622 B2 * | 5/2010 | Tuck ...................... | A61K 48/00 536/23.1 |
| 7,815,911 B1 * | 10/2010 | Straley ................. | A61K 47/646 424/234.1 |
| 8,647,633 B2 | 2/2014 | Heath et al. | |
| 8,795,677 B2 | 8/2014 | Heath et al. | |

FOREIGN PATENT DOCUMENTS

WO    WO2000020039 A1 *   4/2000

OTHER PUBLICATIONS

Impact of Toll-Like Receptor-Specific Agonists on the host immune Response to the Yersinia pestis plague rF1V Vaccine Front Immunol. Aug. 26, 2021. Sec Vaccine and Molecular Therapeutics. vol. 12-2021 (Year: 2021).*
Advanced in preventive medicine, 2012: Article ID 731604, 2012, Hart et. al. (Year: 2012).*
CpG ODNs—TLR9 Agonists InvivoGen https://www.invivogen.com/odn2006-all (2006).*
Heath et al. (Vaccine, vol. 16, No. 11/12, Jul. 1998).*
Anonymous (2021). "Phase II Clinical Trial Demonstrating the Military Utility of a rF1V Vaccine Strategy Consisting of Co-Administration of rF1V with an Established Biological Response Modifier (BRM) Generating of Efficacy and Safety Data," retrieved from the Internet https://sam.gov/opp/074b710fc2334561a016a8c837304530/view, last visited May 5, 2021, 7 pages.
ALHYDROGEL® Adjuvant 2 % (No Date). "Aluminum Hydroxide Gel Version 20J08-MM," Croda/Invivogen, 2 pages.
Biryukov, S. et al. (Aug. 27, 2021). "Impact of Toll-Like Receptor-Specific Agonists on the Host Immune Response to the Yersinia pestis Plague rF1V Vaccine," Frontiers in Immunology and Supplemental 12(726416):1-16, 21 pages.
Braun, R.P. et al. (Sep. 15, 1988). "Immunogenic Duplex Nucleic Acids Are Nuclease Resistant," J Immunol. 141(6):2084-2089.
Campbell, J.D. (2017). "Chapter 2: Development of The CpG Adjuvant 1018: A Case Study," Methods Mol Biol. 1494:15-27.
Coffman, R.L. et al. (Oct. 29, 2010, e-pub. Aug. 16, 2012). "Vaccine Adjuvants: Putting Innate Immunity to Work," Immunity 33(4):492-503, 21 pages.
Genbank AAY23169.1 (Jan. 27, 2006). "Capsule Protein Fraction 1/Virulence Antigen Fusion Protein Precursor [Synthetic Construct]," 2 pages.
Hart, M.K. et al. (2012). "Advanced Development of the rF1V and rBV A/B Vaccines: Progress and Challenges," Advances in Preventive Medicine 2012(731604):1-14, 15 pages.
Hickey, A.J. et al. (2013, e-pub. Apr. 1, 2013). "Intranasal Prophylaxis with CpG Oligodeoxynucleotide Can Protect against Yersinia pestis Infection," Infection an Immunity 81(6):2123-2132.

(Continued)

Primary Examiner — Jennifer E Graser
(74) Attorney, Agent, or Firm — Morrison & Foerster LLP

(57) ABSTRACT

The present disclosure relates to immunogenic compositions comprising at least one *Yersinia pestis* (*Y. pestis*) antigen, an aluminum salt adjuvant, and an oligonucleotide comprising an unmethylated cytidine-phospho-guanosine (CpG) motif. The immunogenic compositions are suitable for stimulating an immune response against *Y. pestis* in a subject in need thereof. The present disclosure also relates to kits and methods using the immunogenic compositions, or two separate compositions which together comprise the antigen, the aluminum salt adjuvant, and the oligonucleotide.

15 Claims, No Drawings
Specification includes a Sequence Listing.

(56) References Cited

OTHER PUBLICATIONS

Hogenesch, H. et al. (2018, e-pub. Oct. 10, 2018). "Optimizing the Utilization of Aluminum Adjuvants in Vaccines: You Might Just Get What You Want," NPJ Vaccines 3:51, 11 pages.

Latimer, L.J.P. et al. (Oct. 1995). "Specificity of Monoclonal Antibodies Produced Against Phosphorothioate and Ribo Modified DNAs," Mol. Immunol. 32(14/15):1057-1064.

Perry, R.D. et al. (Jan. 1997). "Yersinia pestis—Etiologic Agent of Plague," Clin. Microbiol. Rev. 10(1):35-66.

Pramanick, S. et al. (Mar. 2013). "Excipient Selection In Parenteral Formulation Development," Pharma Times 45(3):65-77.

Prentice, M.B. et al. (Apr. 7, 2007). "Plague," Lancet. 369(9568):1196-1207.

Shah, R.R. et al. (2017). "Chapter 1: Overview of Vaccine Adjuvants: Introduction, History, and Current Status," Methods Mol. Biol. 1494:1-13.

* cited by examiner

SEQUENCE LISTING

```
Sequence total quantity: 9
SEQ ID NO: 1            moltype = DNA  length = 22
FEATURE                 Location/Qualifiers
source                  1..22
                        mol_type = other DNA
                        organism = synthetic construct
```

```
misc_feature              1..22
                          note = CpG
SEQUENCE: 1
tgactgtgaa cgttcgagat ga                                             22

SEQ ID NO: 2              moltype = AA   length = 477
FEATURE                   Location/Qualifiers
source                    1..477
                          mol_type = protein
                          organism = synthetic construct
REGION                    1..477
                          note = rF1V
SEQUENCE: 2
ADLTASTTAT ATLVEPARIT LTYKEGAPIT IMDNGNIDTE LLVGTLTLGG YKTGTTSTSV      60
NFTDAAGDPM YLTFTSQDGN NHQFTTKVIG KDSRDFDISP KVNGENLVGD DVVLATGSQD     120
FFVRSIGSKG GKLAAGKYTD AVTVTVSNQE FMIRAYEQNP QHFIEDLEKV RVEQLTGHGS     180
SVLEELVQLV KDKNIDISIK YDPRKDSEVF ANRVITDDIE LLKKILAYFL PEDTILKGGH     240
YDNQLQNGIK RVKEFLESSP NTQWELRAFM AVMHFSLTAD RIDDDILKVI VDSMNHHGDA     300
RSKLREELAE LTAELKIYSV IQAEINKHLS SSGTINIHDK SINLMDKNLY GYTDEEIFKA     360
SAEYKILEKM PQTTIQVDGS EKKIVSIKDF LGSENKRTGA LGNLKNSYSY NKDNNELSHF     420
ATTCSDKSRP LNDLVSQKTT QLSDITSRFN SAIEALNRFI QKYDSVMQRL LDDTSGK       477

SEQ ID NO: 3              moltype = AA   length = 521
FEATURE                   Location/Qualifiers
source                    1..521
                          mol_type = protein
                          organism = synthetic construct
REGION                    1..521
                          note = rF1V-N-tag
SEQUENCE: 3
MGHHHHHHHH HHSSGHIDDD DKHMKKISSV IAIALFGTIA TANAADLTAS TTATATLVEP      60
ARITLTYKEG APITIMDNGN IDTELLVGTL TLGGYKTGTT STSVNFTDAA GDPMYLTFTS     120
QDGNNHQFTT KVIGKDSRDF DISPKVNGEN LVGDDVVLAT GSQDFFVRSI GSKGGKLAAG     180
KYTDAVTVTV SNQEFMIRAY EQNPQHFIED LEKVRVEQLT GHGSSVLEEL VQLVKDKNID     240
ISIKYDPRKD SEVFANRVIT DDIELLKKIL AYFLPEDTIL KGGHYDNQLQ NGIKRVKEFL     300
ESSPNTQWEL RAFMAVMHFS LTADRIDDDI LKVIVDSMNH HGDARSKLRE ELAELTAELK     360
IYSVIQAEIN KHLSSSGTIN IHDKSINLMD KNLYGYTDEE IFKASAEYKI LEKMPQTTIQ     420
VDGSEKKIVS IKDFLGSENK RTGALGNLKN SYSYNKDNNE LSHFATTCSD KSRPLNDLVS     480
QKTTQLSDIT SRFNSAIEAL NRFIQKYDSV MQRLLDDTSG K                         521

SEQ ID NO: 4              moltype = AA   length = 23
FEATURE                   Location/Qualifiers
source                    1..23
                          mol_type = protein
                          organism = synthetic construct
REGION                    1..23
                          note = N-tag [HIS tag + 14 aa linker + enterokinase
                           cleavage site (DDD-K)]
SEQUENCE: 4
MGHHHHHHHH HHSSGHIDDD DKH                                             23

SEQ ID NO: 5              moltype = AA   length = 21
FEATURE                   Location/Qualifiers
source                    1..21
                          mol_type = protein
                          organism = Yersinia pestis
REGION                    1..21
                          note = F1sp
SEQUENCE: 5
MKKISSVIAI ALFGTIATAN A                                               21

SEQ ID NO: 6              moltype = AA   length = 149
FEATURE                   Location/Qualifiers
source                    1..149
                          mol_type = protein
                          organism = Yersinia pestis
REGION                    1..149
                          note = YpF1
SEQUENCE: 6
ADLTASTTAT ATLVEPARIT LTYKEGAPIT IMDNGNIDTE LLVGTLTLGG YKTGTTSTSV      60
NFTDAAGDPM YLTFTSQDGN NHQFTTKVIG KDSRDFDISP KVNGENLVGD DVVLATGSQD     120
FFVRSIGSKG GKLAAGKYTD AVTVTVSNQ                                       149

SEQ ID NO: 7              moltype = AA   length = 326
FEATURE                   Location/Qualifiers
source                    1..326
                          mol_type = protein
                          organism = Yersinia pestis
REGION                    1..326
```

```
                          note = YpV
SEQUENCE: 7
MIRAYEQNPQ HFIEDLEKVR VEQLTGHGSS VLEELVQLVK DKNIDISIKY DPRKDSEVFA    60
NRVITDDIEL LKKILAYFLP EDTILKGGHY DNQLQNGIKR VKEFLESSPN TQWELRAFMA   120
VMHFSLTADR IDDDILKVIV DSMNHHGDAR SKLREELAEL TAELKIYSVI QAEINKHLSS   180
SGTINIHDKS INLMDKNLYG YTDEEIFKAS AEYKILEKMP QTTIQVDGSE KKIVSIKDFL   240
GSENKRTGAL GNLKNSYSYN KDNNELSHFA TTCSDKSRPL NDLVSQKTTQ LSDITSRFNS   300
AIEALNRFIQ KYDSVMQRLL DDTSGK                                       326

SEQ ID NO: 8              moltype = DNA  length = 10
FEATURE                   Location/Qualifiers
source                    1..10
                          mol_type = other DNA
                          organism = synthetic construct
misc_feature              1..10
                          note = 10mer Motif
SEQUENCE: 8
aacgttcgag                                                          10

SEQ ID NO: 9              moltype = DNA  length = 24
FEATURE                   Location/Qualifiers
source                    1..24
                          mol_type = other DNA
                          organism = synthetic construct
misc_feature              1..24
                          note = ODN 2006 aka ODN 7909
SEQUENCE: 9
tcgtcgtttt gtcgttttgt cgtt                                          24
```

IMMUNOGENICITY OF A CPG-ADJUVANTED RECOMBINANT PLAGUE VACCINE

CROSS-REFERENCE TO RELATED APPLICATIONS

This application claims priority to U.S. Provisional Application No. 63/357,542, filed Jun. 30, 2022, the contents of which are hereby incorporated by reference in their entirety for all purposes.

INCORPORATION BY REFERENCE OF SEQUENCE LISTING

The present application is being filed along with a Sequence Listing in electronic format. The Sequence Listing is provided as a file entitled 377882008600SeqList.xml, created Jun. 27, 2023, which is 13,699 bytes in size. The information in the electronic format of the Sequence Listing is incorporated by reference in its entirety.

FIELD

The present disclosure relates to immunogenic compositions comprising at least one *Yersinia pestis* (*Y. pestis*) antigen, an aluminum salt adjuvant, and an oligonucleotide comprising an unmethylated cytidine-phospho-guanosine (CpG) motif. The immunogenic compositions are suitable for stimulating an immune response against *Y. pestis* in a subject in need thereof. The present disclosure also relates to kits and methods using the immunogenic compositions, or two separate compositions which together comprise the antigen, the aluminum salt adjuvant, and the oligonucleotide.

BACKGROUND

Plague is a zoonotic disease caused by infection with the bacterium known as *Yersinia pestis* (*Y. pestis*), which is found in rodents and fleas. Humans can become infected through the bite of an infected flea, or more rarely by inhalation of aerosolized bacteria or by consumption of contaminated meat. Depending on the circumstances of infection, plague can occur in three distinct clinical forms, namely bubonic plague, septicemic plague, and pneumonic plague (Perry et al., Clin Microbiol Rev, 10(1):35-66, 1997; and Prentice et al., Lancet, 369(9568):1196-1207, 2007). Bubonic plague is the most common form of plague and typically occurs as a result of transmission of bacteria to a person's lymph nodes through flea bites. Pneumonic plague occurs as a result of infection of a person's lungs either upon contact with airborne droplets released by a person afflicted with plague or as a complication of bubonic or septicemic plague. Septicemic plague occurs as a result of infection of a person's blood either through bites of infected fleas or as a complication of bubonic or pneumonic plague. Pneumonic plague is the most lethal form of the disease and, if left untreated, leads to respiratory failure and shock.

Historically, plague has resulted in three major pandemics over the last 1,500 years, namely the Justinian Plague, the Black Death, and the Third Plague. It is estimated to have caused over 200 million deaths worldwide. Due to the infectiousness and pathogenicity of *Y. pestis*, there are concerns that pneumonic plague could be developed as a biowarfare or bioterrorism weapon (Hart et al., Advances in Preventive Medicine, 2012: Article ID 731604, 2012). As such, an effective vaccine for protecting military personnel against pneumonic plague is needed.

The one licensed plague vaccine in the United States was a formaldehyde-inactivated, whole cell vaccine (USP vaccine). However, due to concerns over efficacy and reactogenicity, the USP vaccine is no longer available. In the former Soviet Union, a live attenuated plague vaccine (EV76 vaccine) was utilized. But, due to severity of side-effects and potential for reversion to a virulent *Y. pestis* strain, the EV76 vaccine has not been adopted for use in western countries. A subunit vaccine for plague is desirable since it would not require inactivation and would be safer than a live-attenuated vaccine.

In recent years, plague vaccines including one or both of the bacterial capsular Fraction 1 (F1) antigen and the bacterial Virulence (V) antigen have undergone preclinical and clinical testing. The most extensively studied recombinant plague vaccine is the recombinant F1V (rF1V) vaccine, which contains an rF1V fusion protein formulated with an aluminum hydroxide adjuvant. The rF1V vaccine was found to be safe and effective in stimulating antibody responses to the rF1V fusion protein, as well as both the F1 and V antigens (Hart et al., Advances in Preventive Medicine, 2012: Article ID 731604, 2012). However, the use of the rF1V vaccine is hindered by the lengthy administration regimen. Namely, three doses over six months were found to be required to stimulate high titer antibody responses (Hart et al., Advances in Preventive Medicine, 2012: Article ID 731604, 2012).

Thus, there is an unmet need for a safe and effective plague vaccine for stimulating a high titer antibody response against plague antigen(s) in a brief vaccination schedule.

SUMMARY

The present disclosure relates to immunogenic compositions comprising at least one *Yersinia pestis* (*Y. pestis*) antigen, an aluminum salt adjuvant, and an oligonucleotide comprising an unmethylated cytidine-phospho-guanosine (CpG) motif. The immunogenic compositions are suitable for stimulating an immune response against *Y. pestis* in a subject in need thereof. The present disclosure also relates to kits and methods using the immunogenic compositions, or two separate compositions which together comprise the antigen, the aluminum salt adjuvant, and the oligonucleotide.

Provided herein in some embodiments is an immunogenic composition comprising: (i) an unmethylated cytidine-phospho-guanosine (CpG)-containing oligonucleotide comprising the sequence of 5'-TGACTGTGAA CGTTCGAGAT GA-3' (SEQ ID NO:1); (ii) at least one *Yersinia pestis* (*Y. pestis*) antigen; and (iii) an aluminum salt adjuvant, wherein one dose of the immunogenic composition comprises the at least one *Y. pestis* antigen in an amount of from about 32 mcg to about 320 mcg, the oligonucleotide in an amount of from about 750 mcg to about 6000 mcg, and the aluminum salt adjuvant in an amount of from about 250 mcg to about 1250 mcg $Al^{3+}$.

In some of any embodiments, the *Y. pestis* antigen is a recombinant protein comprising an F1 antigen, a V antigen, both an F1 antigen and a V antigen, or an F1V fusion protein.

In some of any embodiments, the *Y. pestis* antigen is a recombinant F1V (rF1V) fusion protein comprising an F1 antigen or fragment thereof and a V antigen or fragment thereof. In some of any embodiments, the F1 antigen comprises the amino acid sequence of SEQ ID NO:6 or an amino acid sequence having at least 90% sequence identity to SEQ ID NO:6, and the V antigen comprises the amino acid sequence of SEQ ID NO:7 or an amino acid sequence having at least 90% sequence identity to SEQ ID NO:7.

In some of any embodiments, the rF1V fusion protein comprises the amino acid sequence of SEQ ID NO:2 or an amino acid sequence having at least 90% sequence identity to SEQ ID NO:2. In some of any embodiments, the rF1V fusion protein comprises the amino acid sequence of SEQ ID NO:2.

In some of any embodiments, the rF1V fusion protein further comprises a signal peptide, the signal peptide comprising the amino acid sequence of SEQ ID NO:5 or an amino acid sequence having at least 90% sequence identity to SEQ ID NO:5.

In some of any embodiments, the oligonucleotide is 22, 23, 24, 25, 26, 27, 28, 29, 30, 31, 32, 33, 34, or 35 nucleotides in length.

In some of any embodiments, the oligonucleotide is a single-stranded oligodeoxynucleotide. In some of any embodiments, the oligonucleotide is fully RNA or is an RNA/DNA chimera.

In some of any embodiments, the oligonucleotide comprises only phosphorothioate linkages, or a combination of one or more phosphodiester linkages and one or more phosphorothioate linkages.

In some of any embodiments, the aluminum salt adjuvant is selected from the group consisting of amorphous aluminum hydroxyphosphate sulfate, aluminum hydroxide, aluminum phosphate, potassium aluminum sulfate, and combinations thereof. In some of any embodiments, the aluminum salt adjuvant is aluminum hydroxide.

In some of any embodiments, the immunogenic composition is a one-dose immunogenic composition.

In some of any embodiments, the one dose of the immunogenic composition comprises the Y. pestis antigen in an amount of about 160 mcg, the oligonucleotide in an amount of about 3000 mcg, and the aluminum salt adjuvant in an amount of about 750 mcg $Al^{3+}$.

In some of any embodiments, the one dose is for administration to a human subject of at least 18 years of age. In some of any embodiments, the human subject is 18-55 years of age.

In some of any embodiments, the immunogenic composition is in liquid form. In some of any embodiments, the immunogenic composition is in lyophilized form.

Also provided herein in some embodiments is a vial comprising any of the provided immunogenic compositions.

Also provided herein in some embodiments is a pre-filled syringe comprising any of the provided immunogenic compositions.

Also provided herein in some embodiments is a kit comprising: a) any of the provided immunogenic compositions, vials, or pre-filled syringes; and b) instructions for administration of the immunogenic composition to a subject to stimulate an immune response against Y. pestis in the subject.

Also provided herein in some embodiments is a kit comprising: a) a first composition comprising an unmethylated cytidine-phospho-guanosine (CpG)-containing oligonucleotide comprising the sequence of 5'-TGACTGTGAA CGTTCGAGAT GA-3' (SEQ ID NO:1); b) a second composition comprising at least one Y. pestis antigen and an aluminum salt adjuvant; and c) instructions for combining the first composition and the second composition to prepare any of the provided immunogenic compositions, wherein one dose of the immunogenic composition comprises the Y. pestis antigen in an amount of from about 32 mcg to about 320 mcg, the oligonucleotide in an amount of from about 750 mcg to about 6000 mcg, and the aluminum salt adjuvant in an amount of from about 250 mcg to about 1250 mcg $Al^{3+}$.

In some of any embodiments, the one dose of the immunogenic composition comprises the Y. pestis antigen in an amount of about 160 mcg, the oligonucleotide in an amount of about 3000 mcg, and the aluminum salt adjuvant in an amount of about 750 mcg $Al^{3+}$.

In some of any embodiments, the kit further comprises: d) a further set of instructions for administration of the immunogenic composition to a subject to stimulate an immune response against Y. pestis in the subject.

In some of any embodiments, the kit further comprises a syringe and needle for intramuscular injection of the immunogenic composition.

Also provided herein in some embodiments is a kit comprising: a) a first composition comprising an unmethylated cytidine-phospho-guanosine (CpG)-containing oligonucleotide comprising the sequence of 5'-TGACTGTGAA CGTTCGAGAT GA-3' (SEQ ID NO:1); b) a second composition comprising at least one Y. pestis antigen and an aluminum salt adjuvant; and c) instructions for separate administration of the first and second compositions to a subject to stimulate an immune response against Y. pestis in the subject; wherein the subject is to be administered the Y. pestis antigen in an amount of from about 32 mcg to about 320 mcg, the oligonucleotide in an amount of from about 750 mcg to about 6000 mcg, and the aluminum salt adjuvant in an amount of from about 250 mcg to about 1250 mcg $Al^{3+}$.

In some of any embodiments, the Y. pestis antigen is an rF1V fusion protein.

In some of any embodiments, the aluminum salt adjuvant is aluminum hydroxide.

In some of any embodiments, the subject is a human subject of at least 18 years of age. In some of any embodiments, the human subject is 18-55 years of age.

Also provided herein in some embodiments is a method for stimulating an immune response against Yersinia pestis in a subject, comprising: administering to a subject a dose of any of the provided immunogenic compositions to stimulate an immune response against Y. pestis in the subject.

In some of any embodiments, the administration is by intramuscular injection.

In some of any embodiments, a first dose and a second dose of the immunogenic composition is administered to the subject.

Also provided herein in some embodiments is a method for stimulating an immune response against Yersinia pestis in a subject, comprising: administering to a subject a first dose and a second dose of any of the provided immunogenic compositions by intramuscular injection to stimulate an immune response against Y. pestis in the subject.

In some of any embodiments, the method further comprises combining a first composition comprising the oligonucleotide and a second composition comprising the Y. pestis antigen and the aluminum salt adjuvant to prepare the immunogenic composition.

In some of any embodiments, the immunogenic composition is a first immunogenic composition, and the second dose is from a second immunogenic composition that is any of the provided immunogenic compositions.

Also provided herein in some embodiments is a method for stimulating an immune response against Yersinia pestis in a subject, comprising: (a) administering to a subject a first dose comprising (i) at least one Y. pestis antigen in an amount of from about 32 mcg to about 320 mcg, (ii) an unmethylated cytidine-phospho-guanosine (CpG)-containing oligonucleotide comprising the sequence of 5'-TGACTGTGAA CGTTCGAGAT GA-3' (SEQ ID NO:1) in an amount of from about 750 mcg to about 6000 mcg, and (iii) an aluminum salt adjuvant in an amount of from about 250 mcg to about 1250 mcg $Al^{3+}$; and (a) administering to the subject a second dose comprising (i) the at least one *Y. pestis* antigen in an amount of from about 32 mcg to about 320 mcg, (ii) the oligonucleotide in an amount of from about 750 mcg to about 6000 mcg, and (iii) the aluminum salt adjuvant in an amount of from about 250 mcg to about 1250 mcg $Al^{3+}$.

In some of any embodiments, the second dose is administered about 1-2 months after administration of the first dose.

Also provided herein in some embodiments is a method for stimulating an immune response against *Yersinia pestis* in a subject, comprising: i) administering to a subject a dose of a first composition comprising an unmethylated cytidine-phospho-guanosine (CpG)-containing oligonucleotide comprising the sequence of 5'-TGACTGTGAA CGTTCGAGAT GA-3' (SEQ ID NO:1), wherein one dose of the first composition comprises the oligonucleotide in an amount of from about 750 mcg to about 6000 mcg; and ii) administering to the subject a dose of a second composition comprising a *Y. pestis* antigen and an aluminum salt adjuvant, wherein one dose of the second composition comprises the *Y. pestis* antigen in an amount of from about 32 mcg to about 320 mcg and the aluminum salt adjuvant in an amount of from about 250 mcg to about 1250 mcg $Al^{3+}$; wherein the first composition and the second composition are separately administered to stimulate an immune response against *Y. pestis* in the subject.

In some of any embodiments, the administration is by intramuscular injection.

In some of any embodiments, a first dose and a second dose of the first composition is administered to the subject, and a first dose and a second dose of the second composition is administered to the subject.

Also provided herein in some embodiments is a method for stimulating an immune response against *Yersinia pestis* in a subject, comprising: i) administering to a subject a first dose and a second dose of a first composition comprising an unmethylated cytidine-phospho-guanosine (CpG)-containing oligonucleotide comprising the sequence of 5'-TGACTGTGAA CGTTCGAGAT GA-3' (SEQ ID NO:1), wherein one dose of the first composition comprises the oligonucleotide in an amount of from about 750 mcg to about 6000 mcg; and ii) administering to the subject a first dose and a second dose of a second composition comprising a *Y. pestis* antigen and an aluminum salt adjuvant, wherein one dose of the second composition comprises the *Y. pestis* antigen in an amount of from about 32 mcg to about 320 mcg and the aluminum salt adjuvant in an amount of from about 250 mcg to about 1250 mcg $Al^{3+}$, wherein the first composition and the second composition are separately administered by intramuscular injection to stimulate an immune response against *Y. pestis* in the subject.

In some of any embodiments, the second dose of the first composition and the second dose of the second composition are administered about 1-2 months after administration of the first dose of the first composition and the first dose of the second composition.

In some of any embodiments, one dose of the first composition comprises the oligonucleotide in an amount of about 3000 mcg, and one dose of the second composition comprises the *Y. pestis* antigen in amount of about 60 mcg and the aluminum salt adjuvant in an amount of about 750 $Al^{3+}$.

In some of any embodiments, the first composition and the second composition are separately administered by intramuscular injection at or near a same injection site. In some of any embodiments, the same injection site is in a same arm, optionally wherein the same injection site is in a deltoid muscle of the same arm.

In some of any embodiments, the *Y. pestis* antigen is an rF1V fusion protein.

In some of any embodiments, the aluminum salt adjuvant is aluminum hydroxide.

In some of any embodiments, the immune response comprises a serum anti-*Y. pestis* antigen concentration of at least about 500 U/mL in the subject at about one month after the second of only two doses of the immunogenic composition or the first and second compositions as determined by an enzyme-linked immunosorbent assay (ELISA). In some of any embodiments, the immune response comprises a serum anti-*Y. pestis* antigen concentration of at least about 750 U/mL in the subject at about one month after the second of only two doses of the immunogenic composition or the first and second compositions as determined by ELISA. In some of any embodiments, the immune response comprises a serum anti-*Y. pestis* antigen concentration of at least about 1000 U/mL in the subject at about one month after the second of only two doses of the immunogenic composition or the first and second compositions as determined by ELISA. In some of any embodiments, the immune response comprises a seroprotective immune response against pneumonic plague at about one month after the second of only two doses of the immunogenic composition or the first and second compositions as determined by a bridge ELISA based on a murine or non-human primate model of pneumonic plague. In some of any embodiments, the immune response comprises a seroprotective immune response against pneumonic plague at about one month after the second of only two doses of the immunogenic composition or the first and second compositions as determined by a protective capacity assay in a murine model of pneumonic plague. In some of any embodiments, the immune response comprises a serum anti-*Y. pestis* antigen concentration at about one month after the second of only two doses of the immunogenic composition or the first and second compositions that is equal to or higher than a serum anti-*Y. pestis* antigen concentration at about one month after a third of only three doses of a comparator composition, wherein the comparator composition comprises the *Y. pestis* antigen in an amount of about 160 mcg and the aluminum salt adjuvant in an amount of about 750 mcg $Al^{3+}$, and wherein the comparator composition does not contain the oligonucleotide. In some of any embodiments, the immune response comprises a serum anti-*Y. pestis* antigen concentration at about one month after the second of only two doses of the immunogenic composition or the first and second compositions that is at least two-fold higher than a serum anti-*Y. pestis* antigen concentration at about one month after a second of only two doses of a comparator composition, wherein the comparator composition comprises the *Y. pestis* antigen in an amount of about 160 mcg and the aluminum salt adjuvant in an amount of about 750 mcg $Al^{3+}$, and wherein the comparator composition does not contain the oligonucleotide. In some of any embodiments, the comparator composition does not comprise any CpG-containing oligonucleotide.

In some of any embodiments, the immune response protects the subject from infection with *Yersinia pestis*.

In some of any embodiments, the immune response prevents the subject from contracting pneumonic plague.

In some of any embodiments, the subject is a human subject of at least 18 years of age. In some of any embodiments, the human subject is 18-55 years of age.

DETAILED DESCRIPTION

The present disclosure relates to immunogenic compositions comprising at least one *Yersinia pestis* (*Y. pestis*) antigen, an aluminum salt adjuvant, and an oligonucleotide comprising an unmethylated cytidine-phospho-guanosine (CpG) motif. The immunogenic compositions are suitable for stimulating an immune response against *Y. pestis* in a subject in need thereof. The present disclosure also relates to kits and methods using the immunogenic compositions, or two separate compositions which together comprise the antigen, the aluminum salt adjuvant, and the oligonucleotide.

General Techniques and Definitions

The practice of the present disclosure will employ, unless otherwise indicated, conventional techniques of molecular biology (including recombinant techniques), microbiology, cell biology, biochemistry, and immunology, which are within the skill of the art.

As used herein and in the appended claims, the singular forms "a", "an", and "the" include plural references unless indicated otherwise. For example, "an" excipient includes one or more excipients.

The phrase "comprising" as used herein is open-ended, indicating that such embodiments may include additional elements. In contrast, the phrase "consisting of" is closed, indicating that such embodiments do not include additional elements (except for trace impurities). The phrase "consisting essentially of" is partially closed, indicating that such embodiments may further comprise elements that do not materially change the basic characteristics of such embodiments.

The term "about" as used herein in reference to a value encompasses from 90% to 110% of that value (e.g., about 3000 mcg of CpG adjuvant refers to 2700 mcg to 3300 mcg of CpG adjuvant).

As used interchangeably herein, the terms "polynucleotide" and "oligonucleotide" include single-stranded DNA (ssDNA), double-stranded DNA (dsDNA), single-stranded RNA (ssRNA), and double-stranded RNA (dsRNA); modified oligonucleotides and oligonucleosides; or combinations thereof. The oligonucleotide can be linearly or circularly configured, or the oligonucleotide can contain both linear and circular segments. Oligonucleotides are polymers of nucleosides joined, generally, through phosphodiester linkages, although alternate linkages, such as phosphorothioate esters, may also be used in oligonucleotides. A nucleoside consists of a purine (adenine (A) or guanine (G) or derivative thereof) or pyrimidine (thymine (T), cytosine (C), or uracil (U), or derivative thereof) base bonded to a sugar. The four nucleoside units (or bases) in DNA are called deoxyadenosine, deoxyguanosine, thymidine, and deoxycytidine. A nucleotide is a phosphate ester of a nucleoside.

The terms "CpG," "CpG motif," and "cytosine-phosphate-guanosine," as used herein, refer to an unmethylated cytidine-phospho-guanosine dinucleotide, which when present in an oligonucleotide contributes to a measurable immune response in vitro, in vivo, and/or ex vivo. Examples of measurable immune responses include, but are not limited to, antigen-specific antibody production, secretion of cytokines, activation or expansion of lymphocyte populations, such as NK cells, CD4+ T lymphocytes, CD8+ T lymphocytes, or B lymphocytes, and the like. Preferably, the CpG-containing oligonucleotide preferentially activates a Th1-type response.

The term "antigen" refers to a substance that is recognized and bound specifically by an antibody or by a T cell antigen receptor. Antigens can include peptides, polypeptides, proteins, glycoproteins, polysaccharides, complex carbohydrates, sugars, gangliosides, lipids, and phospholipids; portions thereof; and combinations thereof. In the context of the present disclosure, the term "antigen" typically refers to a polypeptide or protein antigen at least eight amino acid residues in length, which may comprise one or more post-translational modifications.

The terms "polypeptide" and "protein" are used interchangeably herein to refer to a polymer of amino acid residues, and are not limited to a certain length unless otherwise specified. Polypeptides may include natural amino acid residues or a combination of natural and non-natural amino acid residues. The terms also include post-expression modifications of the polypeptide, for example glycosylation, sialylation, acetylation, phosphorylation, and the like. In some aspects, the polypeptides may contain modifications with respect to a native or natural sequence, as long as the protein maintains the desired activity (e.g., antigenicity).

The terms "isolated" and "purified" as used herein refers to a material that is removed from at least one component with which it is naturally associated (e.g., removed from its original environment). The term "isolated," when used in reference to a recombinant protein, refers to a protein that has been removed from the culture medium of the host cell that produced the protein. In some embodiments, an isolated protein (e.g., *Y. pestis* antigen) is at least 75%, 90%, 95%, 96%, 97%, 98%, or 99% pure as determined by high-performance liquid chromatography (HPLC).

An "effective amount" or a "sufficient amount" of a substance is that amount sufficient to effect beneficial or desired results, including clinical results, and, as such, an "effective amount" depends upon the context in which it is being applied. In the context of administering an immunogenic composition, an effective amount contains sufficient antigen and adjuvant(s) to stimulate an immune response (preferably a seroprotective level of antibody to the antigen).

In the present disclosure, the terms "individual" and "subject" refer to a mammal. "Mammals" include, but are not limited to, humans, non-human primates (e.g., monkeys), farm animals, sport animals, rodents (e.g., mice and rats), and pets (e.g., dogs and cats).

The term "dose" as used herein in reference to an immunogenic composition refers to a measured portion of the immunogenic composition taken by (administered to or received by) a subject at any one time.

"Stimulation" of a response or parameter includes eliciting and/or enhancing that response or parameter when compared to otherwise same conditions except for a parameter of interest, or alternatively, as compared to another condition (e.g., increase in TLR-signaling in the presence of a TLR agonist as compared to the absence of the TLR agonist). For example, "stimulation" of an immune response (e.g., Th1 response) means an increase in the response. Depending upon the parameter measured, the increase may be from 2-fold to 200-fold or over, from 5-fold to 500-fold or over, from 10-fold to 1000-fold or over, or from 2, 5, 10, 50, or 100-fold to 200, 500, 1,000, 5,000, or 10,000-fold.

Conversely, "inhibition" of a response or parameter includes reducing and/or repressing that response or parameter when compared to otherwise same conditions except for a parameter of interest, or alternatively, as compared to another condition (e.g., decrease in bacterial levels in lungs of immunized subjects relative to bacterial levels in lungs of non-immunized subjects). For example, "inhibition" of an immune response (e.g., Th2 response) means a decrease in the response. Depending upon the parameter measured, the decrease may be from 2-fold to 200-fold, from 5-fold to 500-fold or over, from 10-fold to 1000-fold or over, or from 2, 5, 10, 50, or 100-fold to 200, 500, 1,000, 2,000, 5,000, or 10,000-fold.

The relative terms "higher" and "lower" refer to a measurable increase or decrease, respectively, in a response or parameter when compared to otherwise same conditions except for a parameter of interest, or alternatively, as compared to another condition. For instance, a "higher antibody titer" refers to an antigen-reactive antibody titer as a consequence of administration of an immunogenic composition of the present disclosure that is at least 2, 3, 4, 5, 6, 7, 8, 9, or 10-fold above an antigen-reactive antibody titer as a consequence of a control condition (e.g., administration of a comparator composition that is not CpG-adjuvanted, but is otherwise identical to the immunogenic composition). Likewise, a "lower antibody titer" refers to an antigen-reactive antibody titer as a consequence of a control condition (e.g., administration of a comparator composition that is not CpG-adjuvanted, but is otherwise identical to the immunogenic composition) that is at least 2, 3, 4, 5, 6, 7, 8, 9, or 10-fold below an antigen-reactive antibody titer as a consequence of administration of an immunogenic composition of the present disclosure.

As used herein, the term "immunization" refers to a process that increases a mammalian subject's reaction to antigen and therefore improves its ability to resist or overcome infection and/or resist disease.

The term "vaccination" as used herein refers to the introduction of a vaccine into a body of a mammalian subject.

"Adjuvant" refers to a substance which, when added to a composition comprising an antigen, enhances or potentiates an immune response to the antigen in the mammalian recipient upon exposure.

The unit symbol "mcg" used herein refers to micrograms and is equivalent to the unit symbol "µg".

I. Immunogenic Compositions and Kits

The present disclosure relates to immunogenic compositions comprising at least one *Yersinia pestis* (*Y. pestis*) antigen, an unmethylated cytidine-phospho-guanosine (CpG)-containing oligonucleotide, and an aluminum salt adjuvant, wherein the *Y. pestis* antigen, oligonucleotide, and aluminum salt adjuvant are present in the immunogenic composition in amounts effective to stimulate an immune response against the *Y. pestis* antigen in a mammalian subject. In some embodiments, the mammalian subject is a human subject. In some embodiments, the human subject is at least 18 years of age (e.g., an adult), optionally wherein the human subject is about 18 to about 55 years of age.

In certain embodiments, the present disclosure relates to immunogenic compositions comprising: i) an unmethylated cytidine-phospho-guanosine (CpG)-containing oligonucleotide comprising the sequence of 5'-TGACTGTGAA CGTTCGAGAT GA-3'(SEQ ID NO:1); ii) at least one *Y. pestis* antigen; and iii) an aluminum salt adjuvant, wherein one dose of the immunogenic composition comprises the *Y. pestis* antigen in an amount of from about 32 mcg to about 320 mcg, the oligonucleotide in an amount of from about 750 mcg to about 6000 mcg, and the aluminum salt adjuvant in an amount of from about 250 mcg to about 1250 mcg $Al^{3+}$. In exemplary embodiments, the immunogenic compositions comprise i) an unmethylated cytidine-phospho-guanosine (CpG)-containing oligonucleotide comprising the sequence of 5'-TGACTGTGAA CGTTCGAGAT GA-3' (SEQ ID NO:1); ii) at least one *Y. pestis* antigen; and iii) an aluminum salt adjuvant, wherein one dose of the immunogenic composition comprises the *Y. pestis* antigen in an amount of about 160 mcg, the oligonucleotide in an amount of about 3000 mcg, and the aluminum salt adjuvant in an amount of about 750 mcg $Al^{3+}$. In some embodiments, the immunogenic composition is a one-dose immunogenic composition.

In some embodiments, the immunogenic composition is in liquid form. In some embodiments, the immunogenic composition is in lyophilized form.

The present disclosure also relates to vials and pre-filled syringes containing any of the provided immunogenic compositions.

A. Oligonucleotide Toll-Like Receptor 9 (TLR9) Agonists

Toll-like receptors (TLRs) are expressed in and on dendritic cells and other innate immune cells and are among the most important receptors for stimulating a response to the presence of invading pathogens. Humans have multiple types of TLRs that are similar in structure, but recognize different parts of viruses or bacteria. By activating specific TLRs, it is possible to stimulate and control specific types of innate immune responses that can be harnessed to enhance adaptive responses.

TLR9 (CD289) recognizes unmethylated cytidine-phospho-guanosine (CpG) motifs found in microbial DNA, which can be mimicked using synthetic CpG-containing oligodeoxynucleotides (CpG-ODNs). CpG-ODNs are known to enhance antibody production and to stimulate T helper 1 (Th1) cell responses (Coffman et al., Immunity, 33:492-503, 2010). Based on structure and biological function, CpG-ODNs have been divided into three general classes: CpG-A, CpG-B, and CpG-C (Campbell, Methods Mol Biol, 1494:15-27, 2017). The degree of B cell activation varies between the classes, with CpG-A ODNs being weak, CpG-C ODNs being good, and CpG-B ODNs being strong B cell activators. Oligonucleotide TLR9 agonists of the present disclosure are preferably good B cell activators (CpG-C ODN) or more preferably strong (CpG-B ODN) B cell activators.

Optimal oligonucleotide TLR9 agonists often contain a palindromic sequence following the general formula of: 5'-purine-purine-CG-pyrimidine-pyrimidine-3', or 5'-purine-purine-CG-pyrimidine-pyrimidine-CG-3' (U.S. Pat. No. 6,589,940). TLR9 agonism is also observed with certain non-palindromic CpG-enriched phosphorothioate oligonucleotides, but may be affected by changes in the nucleotide sequence. Additionally, TLR9 agonism is abolished by methylation of the cytosine within the CpG dinucleotide. Accordingly in some embodiments, the TLR9 agonist is an oligonucleotide of from 8 to 35 nucleotides in length comprising the sequence 5'-AACGTTCG-3'. In some embodiments, the oligonucleotide is greater than 8, 9, 10, 11, 12, 13, 14, 15, 16, 17, 18, 19, or 20 nucleotides in length, and the oligonucleotide is less than 35, 34, 33, 32, 31, 30, 29, 28, 27, 26, 25, or 24 nucleotides in length. In some embodiments, the TLR9 agonist is an oligonucleotide of from 10 to 35 nucleotides in length comprising the sequence 5'-AACGTTCGAG-3' (SEQ ID NO:8). In some embodiments, the oligonucleotide is greater than 10, 11, 12, 13, 14, 15, 16, 17, 18, 19, or 20 nucleotides in length, and the oligonucleotide is less than 35, 34, 33, 32, 31, 30, 29, 28, 27, 26, 25, or 24 nucleotides in length. Accordingly, in some embodiments, the oligonucleotide does not comprise the sequence 5'-TCGTCGTTTT GTCGTTTTGT CGTT-3' (ODN 2006 or ODN 7909, set forth as SEQ ID NO:9).

Researchers at Dynavax Technologies Corporation (Emeryville, CA) have identified a 22-mer phosphorothioate linked oligodeoxynucleotide, CpG 1018® (CpG ODN 1018) adjuvant, which contains specific sequences that can substantially enhance the immune response to co-administered antigens across species (Campbell, Methods Mol Biol, 1494:15-27, 2017). CpG 1018® (CpG ODN 1018) adjuvant (5'-TGACTGTGAA CGTTCGAGAT GA-3', set forth as SEQ ID NO:1) was chosen after screening a broad panel of oligonucleotides for immunostimulatory activity in vitro and in vivo. CpG 1018® (CpG ODN 1018) adjuvant is a CpG-B ODN that is active in mice, rabbits, dogs, baboons, cynomolgus monkeys, and humans. Thus, in some embodiments, the oligonucleotide is from 22 to 35 nucleotides in length comprising the sequence of SEQ ID NO:1. In certain embodiments, the oligonucleotide is from 22 to 35 nucleotides in length and comprises the sequence 5'-TGACTGT-GAA CGTTCGAGAT GA-3' (SEQ ID NO:1). In certain other embodiments, the oligonucleotide is greater than 22, 23, 24, 25, 26, 27, 28, 29, 30, 31, 32, or 33 nucleotides in length, and the oligonucleotide is less than 35, 34, 33, 32, 31, 30, 29, 28, 27, 26, 25, or 24 nucleotides in length, provided the maximum is below the minimum length. In some embodiments, the oligonucleotide consists of the sequence 5'-TGACTGTGAA CGTTCGAGAT GA-3' (SEQ ID NO:1).

Although the exemplary oligonucleotide, CpG 1018® (CpG ODN 1018) adjuvant, is a CpG-ODN, the present disclosure is not restricted to fully DNA molecules. That is, in some embodiments, the oligonucleotide is a DNA/RNA chimeric molecule in which the CpG(s) and the palindromic sequence are deoxyribonucleic acids and one or more nucleic acids outside of these regions are ribonucleic acids. In some embodiments, the CpG-containing oligonucleotide is linear. In other embodiments, the CpG-containing oligonucleotide is circular or includes hairpin loop(s). In some embodiments, the CpG-containing oligonucleotide is single stranded. In other embodiments, the CpG-containing oligonucleotide is double stranded.

In some embodiments, the CpG-containing oligonucleotide may contain modifications. Modifications include, but are not limited to, modifications of the 3'OH or 5'OH group, modifications of the nucleotide base, modifications of the sugar component, and modifications of the phosphate group. Modified bases may be included in the palindromic sequence of the CpG-containing oligonucleotide as long as the modified base(s) maintains the same specificity for its natural complement through Watson-Crick base pairing (e.g., the palindromic portion is still self-complementary). In some embodiments, the CpG-containing oligonucleotide comprises a non-canonical base. In some embodiments, the CpG-containing oligonucleotide comprises a modified nucleoside. In some embodiments, the modified nucleoside is selected from the group consisting of 2'-deoxy-7-deazaguanosine, 2'-deoxy-6-thioguanosine, arabinoguanosine, 2'-deoxy-2'substituted-arabinoguanosine, and 2'-O-substituted-arabinoguanosine.

The CpG-containing oligonucleotide may contain a modification of the phosphate group. For example, in addition to phosphodiester linkages, phosphate modifications include, but are not limited to, methyl phosphonate, phosphorothioate, phosphoramidate (bridging or non-bridging), phosphotriester, and phosphorodithioate, and may be used in any combination. Other non-phosphate linkages may also be used. In some embodiments, the oligonucleotides comprise only phosphorothioate backbones. In some embodiments, the oligonucleotides comprise only phosphodiester backbones. In some embodiments, the oligonucleotide comprises a combination of phosphate linkages in the phosphate backbone, such as a combination of phosphodiester and phosphorothioate linkages. Oligonucleotides with phosphorothioate backbones can be more immunogenic than those with phosphodiester backbones and appear to be more resistant to degradation after injection into the host (Braun et al., J Immunol, 141:2084-2089, 1988; and Latimer et al., Mol Immunol, 32:1057-1064, 1995). In some embodiments, the CpG-containing oligonucleotides of the present disclosure include at least one, two, or three internucleotide phosphorothioate ester linkages. In some embodiments, when a plurality of CpG-containing oligonucleotide molecules are present in a pharmaceutical composition comprising at least one excipient, both stereoisomers of the phosphorothioate ester linkage are present in the plurality of CpG-containing oligonucleotide molecules. In some embodiments, all of the internucleotide linkages of the CpG-containing oligonucleotide are phosphorothioate linkages, or said another way, the CpG-containing oligonucleotide has a phosphorothioate backbone.

A unit (one) dose of the immunogenic composition may comprise from about 750 mcg to about 6000 mcg of the CpG-containing oligonucleotide, preferably from about 1500 mcg to about 3000 mcg of the CpG-containing oligonucleotide, or preferably about 3000 mcg or about 6000 mcg of the CpG-containing oligonucleotide. In some embodiments, one dose of the immunogenic composition comprises greater than or equal to about 750, 1000, 1250, or 1500 mcg of the CpG-containing oligonucleotide, and less than or equal to about 6000, 5000, 4000, or 3000 mcg of the CpG-containing oligonucleotide. In some embodiments, a one mL dose of the immunogenic composition comprises about 750, 1500, 3000, or 6000 mcg of the CpG-containing oligonucleotide. In some embodiments, one dose of the immunogenic composition comprises about 1500 mcg of the CpG-containing oligonucleotide. In some embodiments, one dose of the immunogenic composition comprises about 3000 mcg of the CpG-containing oligonucleotide. In some embodiments, one dose of the immunogenic composition comprises about 6000 mcg of the CpG-containing oligonucleotide. In some embodiments, one dose is an about 0.25 mL, 0.50 mL, 0.75 mL, or 1.0 mL dose. In some embodiments in which the single (one) dose comprises the CpG-containing oligonucleotide, the antigen, and the aluminum salt adjuvant, the one dose is an about 0.75 mL dose. In some embodiments in which the single (one) dose comprises the CpG-containing oligonucleotide, but does not comprise the antigen and the aluminum salt adjuvant, the one dose is an about 0.25 mL dose. In some embodiments in which the single (one) dose comprises the CpG-containing oligonucleotide and the aluminum salt adjuvant, but does not comprise the antigen, the one dose is an about 0.5 mL dose.

In some embodiments, the CpG-containing oligonucleotides described herein are in their pharmaceutically acceptable salt form. Exemplary basic salts include ammonium salts, alkali metal salts such as sodium, lithium, and potassium salts, alkaline earth metal salts such as calcium and magnesium salts, zinc salts, salts with organic bases (for example, organic amines) such as N-Me-D-glucamine, N-[1-(2,3-dioleoyloxy)propyl]-N,N,N-trimethylammonium chloride, choline, tromethamine, dicyclohexylamines, t-butyl amines, and salts with amino acids such as arginine, lysine, and the like. In some embodiment, the CpG-containing oligonucleotides are in the ammonium, sodium, lithium, or potassium salt form. In certain embodiments, the CpG-containing oligonucleotides are in the sodium salt form.

B. Plague Antigen

A plague antigen of the immunogenic compositions of the present disclosure comprises at least one Yersinia pestis (Y. pestis) antigen or fragment thereof. In some embodiments, the Y. pestis antigen is recognized by Y. pestis-reactive antibodies and/or peptide fragments of Y. pestis are recognized by plague-reactive T cells. In some other embodiments, the Y. pestis antigen is a recombinant protein. In a subset of these embodiments, the Y. pestis antigen is a recombinant fusion protein in which the fusion protein comprises the amino acid sequence of at least two Y. pestis antigens or fragments thereof. In other embodiments, the Y. pestis antigen is a purified antigen obtained from Y. pestis bacteria. In some embodiments, the Y. pestis antigen is a recombinant protein comprising an F1 antigen, a V antigen, both an F1 antigen and a V antigen, or an F1V fusion protein (rF1V fusion protein).

In some embodiments, the Y. pestis antigen comprises an F1 antigen or a fragment thereof, wherein the F1 antigen comprises the amino acid sequence of SEQ ID NO:6 or an amino acid sequence having at least 90%, 95%, 96%, 97%, 98%, or 99% sequence identity to SEQ ID NO:6. In other embodiments, the Y. pestis antigen comprises a V antigen or a fragment thereof, wherein the V antigen comprises the amino acid sequence of SEQ ID NO:7 or an amino acid sequence having at least 90%, 95%, 96%, 97%, 98%, or 99% sequence identity to SEQ ID NO:7. In yet other embodiments, the Y. pestis antigen comprises (i) an F1 antigen or a fragment thereof and a V antigen or a fragment thereof, wherein the F1 antigen comprises the amino acid sequence of SEQ ID NO:6 or an amino acid sequence having at least 90%, 95%, 96%, 97%, 98%, or 99% sequence identity to SEQ ID NO:6, and (ii) the V antigen comprises the amino acid sequence of SEQ ID NO:7 or an amino acid sequence having at least 90%, 95%, 96%, 97%, 98%, or 99% sequence identity to SEQ ID NO:7.

In some embodiments, the Y. pestis antigen is a recombinant protein comprising an F1 antigen or a fragment thereof. In some embodiments, the F1 antigen comprises the amino acid sequence of SEQ ID NO:6 or an amino acid sequence having at least 90%, 95%, 96%, 97%, 98%, or 99% sequence identity to SEQ ID NO:6. In some embodiments, the Y. pestis antigen is a recombinant protein comprising the amino acid sequence of SEQ ID NO:6 or an amino acid sequence having at least 90%, 95%, 96%, 97%, 98%, or 99% sequence identity to SEQ ID NO:6.

In some embodiments, the Y. pestis antigen is a recombinant protein comprising a V antigen or a fragment thereof. In some embodiments, the V antigen comprises the amino acid sequence of SEQ ID NO:7 or an amino acid sequence having at least 90%, 95%, 96%, 97%, 98%, or 99% sequence identity to SEQ ID NO:7. In some embodiments, the Y. pestis antigen is a recombinant protein comprising the amino acid sequence of SEQ ID NO:7 or an amino acid sequence having at least 90%, 95%, 96%, 97%, 98%, or 99% sequence identity to SEQ ID NO:7.

In some embodiments, the Y. pestis antigen is a recombinant protein comprising an F1 antigen or a fragment thereof and a V antigen or a fragment thereof. In some embodiments, the Y. pestis antigen is an rF1V fusion protein.

In some embodiments, the F1 antigen comprises the amino acid sequence of SEQ ID NO:6 or an amino acid sequence having at least 90%, 95%, 96%, 97%, 98%, or 99% sequence identity to SEQ ID NO:6. In some embodiments, the V antigen comprises the amino acid sequence of SEQ ID NO:7 or an amino acid sequence having at least 90%, 95%, 96%, 97%, 98%, or 99% sequence identity to SEQ ID NO:7. In some embodiments, the F1 antigen comprises the amino acid sequence of SEQ ID NO:6 or an amino acid sequence having at least 90%, 95%, 96%, 97%, 98%, or 99% sequence identity to SEQ ID NO:6, and the V antigen comprises the amino acid sequence of SEQ ID NO:7 or an amino acid sequence having at least 90%, 95%, 96%, 97%, 98%, or 99% sequence identity to SEQ ID NO:7.

In some embodiments, the Y. pestis antigen comprises the amino acid sequence of SEQ ID NO:6 or an amino acid sequence having at least 90%, 95%, 96%, 97%, 98%, or 99% sequence identity to SEQ ID NO:6. In some embodiments, the Y. pestis antigen comprises the amino acid sequence of SEQ ID NO:7 or an amino acid sequence having at least 90%, 95%, 96%, 97%, 98%, or 99% sequence identity to SEQ ID NO:7. In some embodiments, the Y. pestis antigen comprises (i) the amino acid sequence of SEQ ID NO:6 or an amino acid sequence having at least 90%, 95%, 96%, 97%, 98%, or 99% sequence identity to SEQ ID NO:6 and (ii) the amino acid sequence of SEQ ID NO:7 or an amino acid sequence having at least 90%, 95%, 96%, 97%, 98%, or 99% sequence identity to SEQ ID NO:7. In some embodiments, the Y. pestis antigen comprises an rF1V fusion protein or a fragment thereof. In some embodiments, the amino acid sequence of the rF1V fusion protein comprises the amino acid sequence of SEQ ID NO:2 or an amino acid sequence having at least 90%, 95%, 96%, 97%, 98%, or 99% sequence identity to SEQ ID NO:2. In some embodiments, the Y. pestis antigen comprises the amino acid sequence of SEQ ID NO:2 or an amino acid sequence having at least 90%, 95%, 96%, 97%, 98%, or 99% sequence identity to SEQ ID NO:2.

In certain embodiments, the Y. pestis antigen further comprises a signal peptide. In some embodiments, the Y. pestis antigen is an rF1V fusion protein that further comprises a signal peptide. In some embodiments, the signal peptide comprises the amino acid sequence of SEQ ID NO:5 or an amino acid sequence having at least 90%, 95%, 96%, 97%, 98%, or 99% sequence identity to SEQ ID NO:5.

In certain embodiments, the Y. pestis antigen further comprises a tag. In some embodiments, the Y. pestis antigen is an rF1V fusion protein that further comprises a tag. In some embodiments, the Y. pestis antigen, e.g., rF1V fusion protein, further comprises a tag and a signal peptide. In some embodiments, the Y. pestis antigen comprises the amino acid sequence of SEQ ID NO:3 or an amino acid sequence having at least 90%, 95%, 96%, 97%, 98%, or 99% sequence identity to SEQ ID NO:3.

In some embodiments, the Y. pestis antigen comprises an rF1V fusion protein or a fragment thereof, wherein the amino acid sequence of the rF1V fusion protein comprises SEQ ID NO:2: ADLTASTTATATLVEPARITLTYKEG-APITIMDNGNIDTELLVGTLTLGGYKTGTTSTS VNF-TDAAGDPMYLTFTSQDGNNHQFTTKVIGKDSR-DFDISPKVNGENLVGDDVVLA TGSQDFFVRSIG-SKGGKLAAGKYTDAVTVTVSNQEFMIRAYEQNPQH-FIEDLEKVRV EQLTGHGSSVLEELVQLVKDKNIDISI-KYDPRKDSEVFANRVITDDIELLKKILAYFLP EDTI-LKGGHYDNQLQNGIKRVKEFLESSPNTQWELRAF-MAVMHFSLTADRIDDDILK VIVDSMNHHGDAR- SKLREELAELTAELKIYSVIQAEINKHLSSSGTINIH-
DKSINLMDK NLYGYTDEEIFKASAEYKILEKMPQT-
TIQVDGSEKKIVSIKDFLGSENKRTGALGNLK NSYS-
YNKDNNELSHFATTCSDKSRPLNDLVSQKTTQL-
SDITSRFNSAIEALNRFIQKY DSVMQRLLDDTSGK. In some embodiments, the rF1V fusion protein comprises an amino acid sequence having at least 90%, 95%, 96%, 97%, 98%, or 99% sequence identity to SEQ ID NO:2. In certain embodiments, the Y. pestis antigen is an rF1V fusion protein which further comprises a signal peptide, and wherein the signal peptide comprises the amino acid sequence of SEQ ID NO:5 or an amino acid sequence having at least 90%, 95%, 96%, 97%, 98%, or 99% sequence identity to SEQ ID NO:5. In certain embodiments, the Y. pestis antigen is an rF1V fusion protein which further comprises a tag and a signal peptide, and wherein the rF1V fusion protein comprises the amino acid sequence of SEQ ID NO:3 or an amino acid sequence having at least 90%, 95%, 96%, 97%, 98%, or 99% sequence identity to SEQ ID NO:3.

As used herein, "percent (%) amino acid sequence identity," "percent identity," and "sequence identity" when used with respect to an amino acid sequence (reference polypeptide sequence) is defined as the percentage of amino acid residues in a candidate sequence (e.g., the subject antigen) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance using publicly available computer software such as BLAST, BLAST-2, ALIGN, or Megalign (DNASTAR) software. Those skilled in the art can determine appropriate parameters for aligning sequences, including any algorithms needed to achieve maximal alignment over the full length of the sequences being compared.

An amino acid substitution may include replacement of one amino acid in a polypeptide with another amino acid. Amino acid substitutions may be introduced into an antigen of interest and the products screened for a desired activity, e.g., increased stability and/or immunogenicity.

Amino acids generally can be grouped according to the following common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro; and
(6) aromatic: Trp, Tyr, Phe.

Conservative amino acid substitutions will involve exchanging a member of one of these classes with another member of the same class. Non-conservative amino acid substitutions will involve exchanging a member of one of these classes with a member of another class.

A unit (one) dose of the immunogenic composition may comprise from about 32 mcg to about 320 mcg of the Y. pestis antigen, preferably from about 40 mcg to about 280 mcg of the Y. pestis antigen, preferably from about 80 mcg to about 240 mcg of the Y. pestis antigen, or preferably from about 120 mcg to about 200 mcg of the Y. pestis antigen. In some embodiments, one dose of the immunogenic composition may comprise about 32 mcg, about 40 mcg, about 85 mcg, about 120 mcg, about 160 mcg, about 200 mcg, about 240 mcg, about 280 mcg, or about 320 mcg of the Y. pestis antigen. In certain embodiments, the one dose comprises about 160 mcg of the Y. pestis antigen. In particular embodiments, one dose is an about 0.25 mL, 0.50 mL, 0.75 mL, or 1.0 mL dose. In some embodiments in which the single (one) dose comprises the CpG-containing oligonucleotide, the antigen, and the aluminum salt adjuvant, the one dose is an about 0.75 mL dose. In some embodiments in which the single (one) dose comprises the antigen and the aluminum salt adjuvant but does not comprise the CpG-containing oligonucleotide, the one dose is an about 0.50 mL dose.

C. Additional Components

The immunogenic compositions of the present disclosure may comprise one or more additional components, such as one or more excipients, additional adjuvants, and/or additional antigens.

1. Excipients

Pharmaceutically acceptable excipients of the present disclosure include, for instance, solvents, bulking agents, buffering agents, tonicity adjusting agents, preservatives, surfactants, and emulsifying agents (Pramanick et al., Pharma Times, 45:65-77, 2013). In some embodiments, the immunogenic compositions may comprise an excipient that functions as one or more of a solvent, a bulking agent, a buffering agent, and a tonicity adjusting agent (e.g., sodium chloride in saline may serve as both an aqueous vehicle and a tonicity adjusting agent). In some embodiments, the immunogenic compositions may comprise an excipient that functions as one or both of a surfactant and an emulsifier (e.g., the nonionic surfactant, polysorbate 80).

In some embodiments, the immunogenic compositions comprise an aqueous vehicle as a solvent. Suitable vehicles include, for instance, sterile water, saline solution, phosphate buffered saline, and Ringer's solution. In some embodiments, the composition is isotonic.

The immunogenic compositions may comprise a buffering agent. Buffering agents control pH to inhibit degradation of the active agent during processing, storage, and optionally reconstitution. Suitable buffers include, for instance, salts comprising acetate, citrate, phosphate, sulfate, or Tris. In certain embodiments, the buffer is not a phosphate-containing buffer. In certain other embodiments, the buffer is a Tris buffer. Other suitable buffers include, for instance, amino acids such as arginine, glycine, histidine, and lysine. The buffering agent may further comprise hydrochloric acid or sodium hydroxide. In some embodiments, the buffering agent maintains the pH of the composition within a range of 6 to 9. In some embodiments, the pH is greater than (lower limit) 6, 7, or 8. In some embodiments, the pH is less than (upper limit) 9, 8, or 7. That is, the pH is in the range of from about 6 to 9 in which the lower limit is less than the upper limit. In some embodiments, the pH is about 6.5, about 7.0, or about 7.5.

The immunogenic compositions may comprise a tonicity adjusting agent. Suitable tonicity adjusting agents include, for instance, dextrose, glycerol, sodium chloride, glycerin, and mannitol.

The immunogenic compositions may comprise a bulking agent. Bulking agents are particularly useful when the pharmaceutical composition is to be lyophilized before administration. In some embodiments, the bulking agent is a protectant that aids in the stabilization and prevention of degradation of the active agents during freeze or spray drying and/or during storage. Suitable bulking agents include, for instance, sugars (mono-, di-, and polysaccharides) such as sucrose, lactose, trehalose, mannitol, sorbital, glucose, and raffinose.

The immunogenic compositions may comprise a preservative. Suitable preservatives include, for instance, antioxidants and antimicrobial agents. However, in some embodiments, the immunogenic composition is prepared under sterile conditions and is in a single use container, and thus does not necessitate inclusion of a preservative.

2. Additional Adjuvants

Adjuvants are known in the art and include, but are not limited to, alum (aluminum salts), oil-in-water emulsions, water-in-oil emulsions, liposomes, and microparticles, such as poly(lactide-co-glycolide) microparticles (Shah et al., Methods Mol Biol, 1494:1-14, 2017). In some embodiments, the immunogenic compositions comprise an aluminum salt adjuvant. In certain embodiments, the immunogenic compositions comprise an aluminum salt to which the at least one *Y. pestis* antigen is adsorbed. In some embodiments, the aluminum salt adjuvant comprises one or more of the group consisting of amorphous aluminum hydroxyphosphate sulfate, aluminum hydroxide, aluminum phosphate, and potassium aluminum sulfate. In particular embodiments, the aluminum salt adjuvant comprises one or both of aluminum hydroxide and aluminum phosphate. In some embodiments, the aluminum salt adjuvant consists of aluminum hydroxide.

A unit (one) dose of the immunogenic composition may comprise from about 250 to about 1250 mcg $Al^{3+}$, preferably from about 500 to about 1000 mcg $Al^{3+}$. In some embodiments, the immunogenic composition comprises about 250 mcg, about 500 mcg, about 750 mcg, about 1000 mcg, or about 1250 mcg $Al^{3+}$. In certain embodiments, the one dose comprises about 750 mcg $Al^{3+}$. In some embodiments, one dose is an about 0.25 mL, 0.50 mL, 0.75 mL, or 1.0 mL dose. In some embodiments in which the single (one) dose comprises the CpG-containing oligonucleotide, the antigen, and the aluminum salt adjuvant, the one dose is an about 0.75 mL dose. In some embodiments in which the single (one) dose comprises the antigen and the aluminum salt adjuvant but does not comprise the CpG-containing oligonucleotide, the one dose is an about 0.50 mL dose.

D. Kits

The present disclosure also provides kits comprising: i) an immunogenic composition comprising at least one *Y. pestis* antigen, a CpG-containing oligonucleotide, and an aluminum salt adjuvant; and ii) a set of instructions for administration of the immunogenic composition to a subject to stimulate an immune response against the at least one *Y. pestis* antigen in the subject. Additionally, the present disclosure provides kits comprising: i) a first composition comprising a CpG-containing oligonucleotide; ii) a second composition comprising at least one *Y. pestis* antigen and an aluminum salt adjuvant; and iii) instructions for combining the first composition with the second composition to prepare an immunogenic composition. In particular embodiments, combining the first composition with the second composition comprises mixing the first and the second compositions, optionally for a maximum of about one hour at room temperature. In some embodiments, combining the first composition with the second composition comprises mixing the first and the second compositions in a single vial, optionally for a maximum of about one hour at room temperature. In certain embodiments, combining the first composition with the second composition comprises mixing the first and the second compositions in a single vial by gentle inversion, optionally for a maximum of about one hour at room temperature In some embodiments, the kits further comprise: iv) further instructions for administration of the immunogenic composition to a subject to stimulate an immune response against the at least one *Y. pestis* antigen in the subject. In certain embodiments, the CpG-containing oligonucleotide comprises the sequence of 5'-TGACTGTGAA CGTTCGAGAT GA-3' (SEQ ID NO:1). In specific embodiments, the subject is a human subject at least 18 years of age (e.g., an adult), optionally wherein the subject is a human subject of about 18 to about 55 years of age. In some embodiments, the oligonucleotide does not comprise the sequence of SEQ ID NO:9.

The present disclosure also provides kits comprising: i) a first composition comprising a CpG-containing oligonucleotide; ii) a second composition comprising at least one *Y. pestis* antigen and an aluminum salt adjuvant; and iii) instructions for separate administration of the first and second compositions to a subject to stimulate an immune response against *Y. pestis* in the subject. In certain embodiments, the CpG-containing oligonucleotide comprises the sequence of 5'-TGACTGTGAA CGTTCGAGAT GA-3' (SEQ ID NO:1). In specific embodiments, the subject is a human subject at least 18 years of age (e.g., an adult), optionally wherein the subject is a human subject of about 18 to about 55 years of age. In some embodiments, the oligonucleotide does not comprise the sequence of SEQ ID NO:9.

In certain embodiments, the kits may comprise an immunogenic composition packaged appropriately. In certain other embodiments, the kits may comprise i) a first composition and ii) a second composition, that are packaged appropriately, such that the first composition and the second composition may be combined to form an immunogenic composition. For example, if the immunogenic composition is a freeze-dried powder, a vial with a resilient stopper is normally used so that the powder may be easily resuspended by injecting fluid (e.g., sterile water, saline, etc.) through the resilient stopper. In some embodiments, the kits comprise a device for administration (e.g., syringe and needle). The instructions relating to the use of the immunogenic composition generally include information as to dosage, schedule, and route of administration for the intended methods of use. In some embodiments, the immunogenic compositions are for stimulating an immune response against the at least one *Y. pestis* antigen in the subject.

The present disclosure also provides kits comprising i) a vial or a pre-filled syringe containing an immunogenic composition comprising at least one *Y. pestis* antigen, a CpG-containing oligonucleotide, and an aluminum salt adjuvant and ii) a set of instructions for administration of the immunogenic composition to a subject to stimulate an immune response against the at least one *Y. pestis* antigen in the subject. In certain embodiments, the CpG-containing oligonucleotide comprises the sequence of 5'-TGACTGT-GAA CGTTCGAGAT GA-3' (SEQ ID NO:1). In specific embodiments, the subject is a human subject at least 18 years of age (e.g., an adult), optionally wherein the subject is a human subject of about 18 to about 55 years of age. In some embodiments, the oligonucleotide does not comprise the sequence of SEQ ID NO:9.

In some embodiments where the kit comprises a first composition and a second composition, either or both of the first and second compositions is contained in a vial or a pre-filled syringe. In some embodiments, either or both of the first and second compositions is in liquid form. In some embodiments, either or both of the first and second compositions is in lyophilized form. In some embodiments, at least one of the first and second compositions is in liquid form. In some embodiments, the kit further comprises a pharmaceutically acceptable carrier, e.g., in a separate vial or syringe.

In some embodiments, the instructions are for preparing a liquid form of the immunogenic composition. In some embodiments, a pharmaceutically acceptable carrier included in the kit, e.g., in a separate vial or syringe, is used to prepare a liquid form of the immunogenic composition. In some embodiments, the instructions are for administering a liquid form of the immunogenic composition.

In some embodiments, the kit includes instructions for preparing liquid forms of the first and second compositions. In some embodiments, a pharmaceutically acceptable carrier included in the kit, e.g., in a separate vial or syringe, is used to prepare liquid forms of the first and second compositions. In some embodiments, the instructions are for administering liquid forms of the first and second compositions.

The immunogenic compositions, CpG-containing oligonucleotides, *Y. pestis* antigens, and aluminum salt adjuvants contained in the provided kits can be any described herein, for instance in Section I-A to I-C. In some embodiments, the administration of the immunogenic composition, first composition, and/or second composition is according to any of the methods described herein, for instance in Section II.

II. Methods of Use

The present disclosure also relates to methods for stimulating an immune response against *Yersinia pestis* (*Y. pestis*) in a subject. In some embodiments, the immune response prevents the subject from infection with *Yersinia pestis*. In some embodiments, the immune response prevents the subject from contracting pneumonic plague. In some embodiments, the immune response prevents or further prevents the subject from contracting one or both of bubonic plague and septicemic plague.

In some embodiments, the subject is a human subject at least 18 years of age (e.g., an adult), optionally wherein the human subject is about 18 to about 55 years of age.

In some embodiments, the method comprises administering to a subject a dose of an immunogenic composition comprising at least one *Y. pestis* antigen, a CpG-containing oligonucleotide, and an aluminum salt adjuvant. In some embodiments, the administration is by intramuscular injection, such as by using a syringe.

In some embodiments, multiple doses of an immunogenic composition comprising at least one *Y. pestis* antigen, a CpG-containing oligonucleotide, and an aluminum salt adjuvant are administered to the subject. In some embodiments, a first dose and a second dose of an immunogenic composition comprising at least one *Y. pestis* antigen, a CpG-containing oligonucleotide, and an aluminum salt adjuvant are administered to the subject. In some embodiments, the multiple doses are from the same immunogenic composition. In some embodiments, the multiple doses are from separate immunogenic compositions that each comprise at least one *Y. pestis* antigen, a CpG-containing oligonucleotide, and an aluminum salt adjuvant.

In some embodiments, the method comprises combining a first composition comprising the oligonucleotide and a second composition comprising the *Y. pestis* antigen and the aluminum salt adjuvant to prepare the immunogenic composition prior to administration. In some embodiments, the method comprises such a combining step to prepare each of the separate immunogenic compositions containing the multiple doses. In some embodiments, a liquid form of the immunogenic composition is prepared and administered. In some embodiments, a pharmaceutically acceptable carrier is used to prepare a liquid form of the immunogenic composition.

In some embodiments, the method comprises administering to the subject a dose of a first composition comprising a CpG-containing oligonucleotide and a dose of a second composition comprising at least one *Y. pestis* antigen and an aluminum salt adjuvant, wherein the first composition and the second composition are separately administered. In some embodiments, both of the separate administrations are by intramuscular injection, such as by using a syringe. The first and second compositions can be administered to the subject in either order. In some embodiments, liquid forms of the first and second composition compositions are prepared and administered. In some embodiments, a pharmaceutically acceptable carrier is used to prepare liquid forms of the first and second compositions.

In some embodiments, multiple doses of one or both of the first and second compositions are administered to the subject. In some embodiments, a first dose and a second dose of the first composition are administered to the subject. In some embodiments, a first dose and a second dose of the second composition are administered to the subject.

In some embodiments, the multiple doses of the first composition are from the same composition. In some embodiments, the multiple doses of the first composition are from separate compositions each comprising a CpG-containing oligonucleotide.

In some embodiments, the multiple doses of the second composition are from the same composition. In some embodiments, the multiple doses of the second composition are from separate compositions each comprising at least one *Y. pestis* antigen and an aluminum salt adjuvant.

The present disclosure also relates to methods for stimulating an immune response against *Yersinia pestis* (*Y. pestis*) in a subject, comprising: administering to the subject a first dose and a second dose of an immunogenic composition comprising at least one *Y. pestis* antigen, a CpG-containing oligonucleotide, and an aluminum salt adjuvant, wherein the immunogenic composition is administered by intramuscular injection to stimulate an immune response against the *Y. pestis* antigen in the subject. The present disclosure also relates to methods for stimulating an immune response against *Yersinia pestis* (*Y. pestis*) in a subject, comprising: i) administering to the subject a first dose and a second dose of a first composition comprising a CpG-containing oligonucleotide, and ii) administering to the subject a first dose and a second dose of a second composition comprising at least one *Y. pestis* antigen and an aluminum salt adjuvant, wherein the first composition and the second composition are separately administered by intramuscular injection to stimulate an immune response against the *Y. pestis* antigen in the subject. The present disclosure also relates to methods for stimulating an immune response against *Yersinia pestis* (*Y. pestis*) in a subject, comprising: i) administering to the subject a first dose and a second dose of a second composition comprising at least one *Y. pestis* antigen and an aluminum salt adjuvant; and ii) administering to the subject a first dose and a second dose of a first composition comprising a CpG-containing oligonucleotide, wherein the first composition and the second composition are separately administered by intramuscular injection to stimulate an immune response against the *Y. pestis* antigen in the subject. That is, in the methods of the present disclosure involving separate administration of two compositions, the composition comprising a CpG-containing oligonucleotide can be administered before or after administration of the composition comprising the at least one *Y. pestis* antigen and the aluminum salt adjuvant. In some embodiments, the CpG-containing oligonucleotide comprises the sequence of 5'-TGACTGTGAA CGTTCGAGAT GA-3' (SEQ ID NO:1). In some embodiments, the subject is a human subject at least 18 years of age (e.g., an adult), optionally wherein the human subject is about 18 to about 55 years of age. In some embodiments, the oligonucleotide does not comprise the sequence of SEQ ID NO:9.

Stimulating an immune response means increasing the immune response, which can arise from eliciting a de novo immune response (e.g., as a consequence of an initial vaccination regimen) or enhancing an existing immune response (e.g., as a consequence of a booster vaccination regimen). In some embodiments, stimulating an immune response includes but is not limited to one or more of the group consisting of: stimulating cytokine production; stimulating B lymphocyte proliferation; stimulating antibody production; stimulating interferon pathway-associated gene expression; stimulating chemoattractant-associated gene expression; and stimulating plasmacytoid dendritic cell maturation.

In some embodiments, the methods of the present disclosure are suitable for increasing the immune response against the at least one *Y. pestis* antigen in the subject relative to a baseline immune response against the at least one *Y. pestis* antigen in the subject prior to administration of the immunogenic composition. In some embodiments, the immune response comprises a serum anti-*Y. pestis* antigen, e.g., anti-rF1V, concentration of at least about 500 U/mL, about 750 U/mL, or about 1000 U/mL in the subject at about one month after the second of only two doses of the immunogenic composition or after the second of only two doses of the first and second compositions as determined by an enzyme-linked immunosorbent assay (ELISA). In some embodiments, the immune response comprises a seroprotective immune response against pneumonic plague at about one month after the second of only two doses of the immunogenic composition or the first and second compositions as determined by a bridge ELISA based on a murine or non-human primate model of pneumonic plague. In some embodiments, the immune response comprises or further comprises a seroprotective immune response against one or both of bubonic plague and septicemic plague at about one month after the second of only two doses of the immunogenic composition or the first and second compositions as determined by a bridge ELISA based on an appropriate animal model. In some embodiments, the immune response comprises a seroprotective immune response against pneumonic plague at about one month after the second of only two doses of the immunogenic composition or the first and second compositions as determined by a protective capacity assay in a murine model of pneumonic plague. In some embodiments, the immune response comprises a serum anti-*Y. pestis* antigen, e.g., anti-rFTV, concentration at about one month after the second of only two doses of the immunogenic composition or the first and second compositions that is higher than a serum anti-*Y. pestis* antigen, e.g., anti-rFTV, concentration at about one month after a third of only three doses of a comparator composition, wherein the comparator composition comprises the *Y. pestis* antigen, e.g., rFTV fusion protein, and the aluminum salt adjuvant, e.g., aluminum hydroxide, in the same amounts as the immunogenic composition or the first and second compositions, and wherein the comparator composition does not contain the oligonucleotide. In some embodiments, the immune response comprises a serum anti-*Y. pestis* antigen, e.g., anti-rFTV, concentration at about one month after the second of only two doses of the immunogenic composition or the first and second compositions that is at least two-fold higher than a serum anti-*Y. pestis* antigen, e.g., anti-rFTV, concentration at about one month after a second of only two doses of a comparator composition, wherein the comparator composition comprises the *Y. pestis* antigen, e.g., rFTV fusion protein, and the aluminum salt adjuvant, e.g., aluminum hydroxide, in the same amounts as the immunogenic composition or the first and second compositions, and wherein the comparator composition does not contain the oligonucleotide. In some embodiments, the comparator composition does not comprise any CpG-containing oligonucleotide. In some embodiments, the immune response prevents the subject from infection with *Yersinia pestis*. In some embodiments, the immune response prevents the subject from contracting pneumonic plague. In some embodiments, the immune response prevents or further prevents the subject from contracting one or both of bubonic plague and septicemic plague.

In some embodiments, the first composition and the second composition are separately administered by intramuscular injection at or near a same injection site. In some embodiments, the injection site for the separate injections is in a same arm, optionally wherein the same injection site is in a deltoid muscle of the same arm. In some embodiments, the first and second compositions are separately injected within about 3 inches, within about 2 inches, or within about 1 inch of one another. In some embodiments, the first and second compositions are separately injected about 1 inch from one another.

In some embodiments, the first composition and the second composition are separately administered, in either order, within a predetermined time period of each other. In some embodiments, the first and second compositions are administered in either order within about 20 minutes, within about 15 minutes, within about 10 minutes, within about 5 minutes, or within about 2 minutes of each other. In some embodiments, whichever composition is administered second is administered immediately following the previously administered composition. In some embodiments, the first and second compositions are administered simultaneously or substantially simultaneously.

In some methods of the present disclosure, a first dose and a second dose of the immunogenic composition (or the first composition and the second composition) is administered to the subject, with the second dose administered from about 1 month to about 3 months after the first dose. In some embodiments, the second dose is administered about 1 month after the first dose. In some embodiments, the second dose is administered about 2 months after the first dose.

The immunogenic compositions, CpG-containing oligonucleotides, *Y. pestis* antigens, and aluminum salt adjuvants administered as part of the provided methods can be any described herein, for instance in Section I-A to I-C. The first and second compositions administered or used for preparing the immunogenic composition as part of the provided methods can be any described herein, for instance in Section I-D.

EXAMPLES

Abbreviations: CMI (cell-mediated immunity); CpG (unmethylated cytidine-phospho-guanosine); CTRL (control); GMC (geometric mean concentration); IFNγ (interferon-gamma); IL-2 (interleukin-2); IM (intramuscular); mcg (microgram); mL (milliliter); PBMC (peripheral blood mononuclear cell); TLR9 (toll-like receptor 9); and TNFα (tumor necrosis factor-alpha).

Example 1

Immunogenicity, Safety, and Tolerability of a Recombinant Plague Vaccine in the Presence or Absence of a CpG-Adjuvant in Human Subjects This example provides a description of an on-going phase II clinical trial being conducted in healthy adults to compare effects of administration of two doses of a recombinant plague vaccine (rF1V vaccine) comprising or co-administered with CpG adjuvant to administration of three doses of the rF1V vaccine in the absence of CpG adjuvant.

Vaccines: The CpG adjuvant was CpG 1018® (CpG ODN 1018) adjuvant (Dynavax Technologies Corporation, Emeryville, CA), which is a phosphorothioate-linked oligodeoxynucleotide, TLR9 agonist. The nucleotide sequence of the CpG 1018® (CpG ODN 1018) adjuvant is set forth as (SEQ ID NO:1). The plague antigen was a recombinant fusion protein including a F1 capsular protein antigen of *Yersinia pestis* fused to the V virulence antigen of *Yersinia pestis* via a short linker sequence (rF1V fusion protein), which was produced in *E. coli*. The amino acid sequence of the rF1V fusion protein devoid of the F1 signal sequence is set forth as SEQ ID NO:2. The rF1V vaccine was formulated with an aluminum hydroxide adjuvant, Alhydrogel® (aluminum hydroxide gel) adjuvant (manufactured by Croda International Plc, UK, and distributed by InvivoGen, San Diego, CA). One dose of the rF1V vaccine contained 160 mcg rF1V and 750 mcg alum. One dose of the CpG adjuvant contained 3000 mcg of CpG 1018® (CpG ODN 1018) adjuvant.

Primary Objectives: To select one of the two methods of administration of rF1V vaccine with CpG 1018® (CpG ODN 1018) adjuvant by comparing humoral immunization response 28 days after the second dose of vaccine. To assess the utility of a 2-dose schedule of rF1V vaccine with CpG 1018® (CpG ODN 1018) adjuvant as measured by reduction in time to onset of predicted rF1V protection. To assess the serum Bridge ELISA antibody concentration to rF1V with CpG 1018® (CpG ODN 1018) adjuvant compared with rF1V vaccine 28 days after the second dose of vaccine.

Secondary Objectives: To assess the safety and tolerability of rF1V vaccine with CpG 1018® (CpG ODN 1018) adjuvant compared with rF1V vaccine. To assess the safety and tolerability of rF1V vaccine with CpG 1018® (CpG ODN 1018) adjuvant compared with rF1V vaccine. To assess the serum Bridge ELISA concentration to rF1V with CpG 1018® (CpG ODN 1018) adjuvant at selected time points after each dose.

All subjects are being monitored for safety through Day 392. Safety assessments include the following: assessment of post-injection local and systemic reaction (for 7 days post each injection); adverse events assessments; vital signs measurements; and physical examinations.

Exploratory Objectives: To assess long term clinical benefit from rF1V vaccine with CpG 1018® (CpG ODN 1018) adjuvant compared with rF1V vaccine. To assess the utility of a 2-dose schedule of rF1V vaccine with CpG 1018® (CpG ODN 1018) adjuvant as measured by reduction in time to onset of predicted rF1V protection using peak serum Bridge ELISA concentration. To assess the peak serum bridge ELISA concentration from rF1V with CpG 1018® (CpG ODN 1018) adjuvant compared with rF1V vaccine 28 days after the complete series.

Study Design. The on-going study is a phase 2, randomized, placebo-controlled, subject and observer-blinded, multicenter trial of the immunogenicity, safety, and tolerability of rF1V vaccine with CpG 1018® (CpG ODN 1018) adjuvant compared with rF1V vaccine alone in adults. Healthy adults 18 to 55 years of age were enrolled to compare a two-dose regimen of rF1V with CpG 1018® (CpG ODN 1018) adjuvant for administration on study Days 1 and 29 (and placebo at Day 183) with a three-dose regimen of rF1V vaccine alone for administration on study Days 1, 29, and 183.

When investigational product or placebo was co-administered as 2 separate injections, the injections were administered in close physical proximity to each other (within approximately 1 inch).

For Part 1 of the study (see Table 1-1), there were 2 administration methods of rF1V vaccine with CpG 1018® (CpG ODN 1018) adjuvant. For subjects in Group 1, rF1V vaccine and CpG 1018® (CpG ODN 1018) adjuvant were co-administered as 2 separate injections on Days 1 and 29, and 2 injections of placebo were administered on Day 183. For subjects in Group 2, a bedside mix of rF1V vaccine+ CpG 1018® (CpG ODN 1018) adjuvant (bedside mix was administered as 1 injection) and placebo were administered as 2 separate injections on Days 1 and 29, and 2 separate injections of placebo were administered on Day 183.

In addition, rF1V vaccine was administered alone without CpG 1018® (CpG ODN 1018) adjuvant; subjects in Group 3 received rF1V vaccine and placebo administered as 2 separate injections on Days 1, 29, and 183. All Groups received 2 injections at each treatment visit to maintain the blind.

A preferred method from Groups 1 and 2 was selected upon review of Day 57 immunogenicity data. The preferred method was expected, 1 month after 2 doses of rF1V vaccine with CpG 1018® (CpG ODN 1018) adjuvant, to result in a GMC that was at least 2 times higher than the GMC of Group 3 one month after 2 doses of rF1V vaccine without CpG 1018® (CpG ODN 1018) adjuvant.

The preferred method having been determined, outcomes from subjects receiving administration of the rF1V vaccine with CpG 1018® (CpG ODN 1018) adjuvant using said method are being compared to outcomes from Group 3, subjects receiving rF1V vaccine co-administered with placebo. Subjects are being followed through Day 393 (Week 56).

Study Population. Healthy adult subjects or adult subjects with stable medical conditions who were 18-55 years of age were selected for inclusion. Typical exclusion criteria applied, including but not limited to a history of plague disease or having previously received any plague vaccine; active tuberculosis or other systemic infectious disease; history of immunodeficiency; history of autoimmune disorder; history of sensitivity to any component of study vaccines; body mass index≥30 kg/m$^2$; having received a COVID-19 vaccine within 14 days, or any other vaccine within 28 days of injection; recent use of systemic corticosteroids or other immunomodulators with the exception of inhaled steroids; undergoing chemotherapy or expected to receive chemotherapy; or an oral temperature above 100.0° F. at the time of vaccine administration.

Study Treatments. Treatments are described below and shown in Tables 1-1 and 1-2.

For Part 1 of the study (see Table 1-1), and for subjects in Group 1, 2 injections of 1) 0.5 mL of rF1V vaccine (160 mcg rF1V+750 mcg alum), and 2) 0.25 mL of CpG 1018® (CpG ODN 1018) adjuvant (3000 mcg) were administered intramuscularly in the deltoid muscle of the non-dominant arm on Days 1 and 29, and 2 injections of 0.25 mL placebo (normal saline) were administered on Day 183.

For subjects in Group 2, 2 injections of 1) 0.75 mL of the bedside mix of rF1V vaccine and CpG 1018® (CpG ODN 1018) adjuvant (0.5 mL and 0.25 mL respectively), and 2) 0.25 mL of placebo were administered intramuscularly in the deltoid muscle of the non-dominant arm on Days 1 and 29, and 2 injections of 0.25 mL placebo were administered on Day 183.

For subjects in Group 3, 2 injections of 1) 0.5 mL of rF1V vaccine, and 2) 0.25 mL of placebo were administered intramuscularly in the deltoid muscle of the non-dominant arm on Days 1, 29, and 183.

The bedside mixture of rF1V vaccine and CpG 1018® (CpG ODN 1018) adjuvant administered to Group 2 was shown to outperform the separate injections administered to Group 1 (see Tables 1-3 and 1-4). For Part 2 of the study (see Table 1-2), incoming subjects are being administered a single injection intramuscularly in the deltoid muscle on Days 1, 29, and 183, consisting of either (i) 0.75 mL of the bedside mixture on Days 1 and 29 and 0.25 mL of placebo on Day 183 (Group 2) or (ii) 0.5 mL of rF1V vaccine on all three days (Group 3).

If the separate injections of rF1V vaccine and CpG 1018® (CpG ODN 1018) adjuvant administered to Group 1 had been shown to outperform the bedside mixture administered to Group 2, then incoming subjects for Part 2 would have continued to be administered two injections intramuscularly in the deltoid muscle on Days 1, 29, and 183, consisting of either (i) 0.5 mL of rF1V vaccine and 0.25 CpG on Days 1 and 29, and 2×0.25 mL of placebo on Day 183 (Group 1) or (ii) 0.5 mL of rF1V vaccine and 0.25 mL placebo on all three days (Group 3).

TABLE 1-1

| Study Treatments - Part 1 | | | |
|---|---|---|---|
| Part 1 | Dose 1 (Day 1) | Dose 2 (Day 29) | Dose 3 (Day 183) |
| Group 1 rF1V vaccine and CpG co-administration | | | |
| Injection 1 | 0.5 mL rF1V | 0.5 mL rF1V | 0.25 mL placebo |
| Injection 2 | 0.25 mL CpG | 0.25 mL CpG | 0.25 mL placebo |
| Total | 0.75 mL | 0.75 mL | 0.5 mL |
| Group 2 rF1V vaccine + CpG bedside mix | | | |
| Injection 1 | 0.75 mL rF1V + CpG | 0.75 mL rF1V + CpG | 0.25 mL placebo |
| Injection 2 | 0.25 mL placebo | 0.25 mL placebo | 0.25 mL placebo |
| Total | 1.0 mL | 1.0 mL | 0.5 mL |
| Group 3 rF1V vaccine | | | |
| Injection 1 | 0.5 mL rF1V | 0.5 mL rF1V | 0.5 mL rF1V |
| Injection 2 | 0.25 mL placebo | 0.25 mL placebo | 0.25 mL placebo |
| Total | 0.75 mL | 0.75 mL | 0.75 mL |

TABLE 1-2

| Study Treatments - Part 2 | | | | |
|---|---|---|---|---|
| Part 2 | | Dose 1 (Day 1) | Dose 2 (Day 29) | Dose 3 (Day 183) |
| Scenario 1 (Group 1 and 3) | Group 1 rF1V vaccine and CpG co-administration | | | |
| | Injection 1 | 0.5 mL rF1V | 0.5 mL rF1V | 0.25 mL placebo |
| | Injection 2 | 0.25 mL CpG | 0.25 mL CpG | 0.25 mL placebo |
| | Total | 0.75 mL | 0.75 mL | 0.5 mL |
| | Group 3 rF1V vaccine | | | |
| | Injection 1 | 0.5 mL rF1V | 0.5 mL rF1V | 0.5 mL rF1V |
| | Injection 2 | 0.25 mL placebo | 0.25 mL placebo | 0.25 mL placebo |
| | Total | 0.75 mL | 0.75 mL | 0.75 mL |
| OR | | | | |
| Scenario 2 (Group 2 and 3) | Group 2 rF1V vaccine + CpG bedside mix | | | |
| | Injection | 0.75 mL rF1V + CpG | 0.75 mL rF1V + CpG | 0.25 mL placebo |
| | Group 3 rF1V vaccine | | | |
| | Injection | 0.5 mL rF1V | 0.5 mL rF1V | 0.5 mL rF1V |

Immunogenicity Assessments. All analyses of demographics, medical history, and safety are being summarized in a descriptive manner. In general, continuous variables are being summarized by number of subjects, mean, standard deviation, median, quartiles, minimum, and maximum. Categorical variables are being summarized by number and percentage of subjects in each study group as appropriate.

Three patient populations are being considered for the immunogenicity analyses: the Safety Population, the modified Intent-To-Treat (mITT) Population, and the Per-Protocol (PP) Population. The Safety Population comprises all subjects who received at least 1 dose of the study vaccine, excluding subjects who had no on-study data. The mITT population for the immunogenicity analysis comprises all eligible subjects who received at least 1 dose of study vaccine and had a post-injection immunogenicity evaluation. The PP population for the immunogenicity analyses comprises Groups 1 and 2 subjects who received 2 doses of study vaccine and Group 3 subjects who received 3 doses of study vaccine, had no major protocol violations, and had immunogenicity data obtained within the study visit windows at Day 57 for Groups 1 and 2 and Day 211 for Group 3.

The primary and other immunogenicity endpoints are being analyzed using the mITT population. Sensitivity analyses on immunogenicity data are also being presented using the PP population. Immunogenicity is being measured by serum rF1V Bridge ELISA concentration at each visit when blood is collected.

After Day 57, immunogenicity data became available to determine whether the GMC 1 month after 2 doses of rF1V vaccine with CpG 1018® (CpG ODN 1018) adjuvant using either the Group 1 or Group 2 administration method was at least 2 times higher than the GMC 1 month after 2 doses of rF1V vaccine in Group 3, after which the administration method of vaccine used for the remainder of the trial was selected.

Bridge ELISA. The immunoassays are using one or more of rF1, rV, and rF1V antigens to evaluate the humoral immune response to rF1V vaccination, using a single standard curve that allows direct comparison across clinical (human) and nonclinical (animal models such as mice, rats, and/or monkeys) samples (see, Section 6.3 of Hart et al., Advances in Preventive Medicine, 2012: Article ID 731604, 2012, which is herein incorporated by reference). The assays are based on the capture of reactive antibodies in immune sera using plates coated with recombinant his-tagged antigen (his-F1, his-V, or his-F1V). The bound antibodies are being detected by adding diluted biotinylated antigen (rF1, rV, or rF1V) followed by horseradish peroxidase-conjugated streptavidin solutions and tetramethylbenzidine substrate. A chicken IgY standard curve is being used to quantitate the levels of antibody to rF1, rV, and rF1V in the tested serum.

Tables 1-3 and 1-4 show rF1V Bridge ELISA results for blood samples collected on Day 1, Week 4, Week 8, Week 12, and Week 16 visits for the mITT population. Results shown are based on serum rF1V Bridge ELISA GMCs by vaccine group (Group 1, Group 2, or Group 3), with 95% confidence intervals (CI) also shown.

TABLE 1-3

| Bridge ELISA GMCs | | | | | | |
|---|---|---|---|---|---|---|
| | Group 1 CpG Co-Administration | | Group 2 CpG Bedside Mix | | Group 3 rF1V Only | |
| Visit | N | GMC (95% CI) | N | GMC (95% CI) | N | GMC (95% CI) |
| Day 1 | 21 | 5.0 (NE-NE) | 20 | 5.0 (NE-NE) | 19 | 5.5 (4.5-6.8) |
| Week 4 | 21 | 102.1 (35.7-292.3) | 20 | 115.8 (50.9-263.4) | 19 | 24.3 (5.8-101.7) |
| Week 8 | 21 | 497.8 (250.1-991.0) | 20 | 766.8 (479.5-1226.2) | 18 | 75.3 (23.3-243.4) |
| Week 12 | 21 | 459.6 (236.1-894.8) | 19 | 620.3 (393.0-979.0) | 18 | 91.3 (30.8-270.7) |
| Week 16 | 20 | 539.5 (290.9-1000.7) | 18 | 742.0 (496.6-1108.6) | 18 | 102.2 (35.3-296.4) |

NE: Non-existent

TABLE 1-4

| Bridge ELISA GMC Ratios | | |
|---|---|---|
| | GMC Ratio (95% CI) | |
| Visit | Group 1 (CpG Co-Administration)/ Group 3 (rF1V Only) | Group 2 (CpG Bedside Mix)/ Group 3 (rF1V Only) |
| Day 1 | 0.9 (0.7-1.1) | 0.9 (0.7-1.1) |
| Week 4 | 4.2 (0.8-22.8) | 4.8 (1.0-22.9) |
| Week 8 | 6.6 (1.9-23.5) | 10.2 (3.2-32.8) |
| Week 12 | 5.0 (1.5-16.6) | 6.8 (2.2-20.7) |
| Week 16 | 5.3 (1.7-16.8) | 7.3 (2.4-21.7) |

As shown in Tables 1-3 and 1-4, anti-rF1V antibody levels remained stable from Week 8 to Week 16. At Week 16, the GMC ratio between Group 1 (CpG adjuvant co-administration) and Group 3 (rF1V vaccine only) was 5.3, and the GMC ratio between Group 2 (CpG adjuvant bedside mix) and Group 3 (rF1V vaccine only) was 7.3. Together, these results indicate improved immunogenicity with administration of the CpG adjuvant, with the most improvement observed when a bedside mix of rF1V vaccine and CpG adjuvant was administered in a single injection.

A Bridge ELISA threshold that corresponds to 50% predicted vaccine efficacy after 2 doses of rF1V vaccine with CpG 1018® (CpG ODN 1018) adjuvant is being obtained from a model using Bridge ELISA data after 3 doses of rF1V vaccine in this study. Predicted protection rate (percentage of subjects reaching the Bridge ELISA threshold) and associated 95% two-sided Clopper-Pearson confidence intervals are being computed. Fisher's exact tests are being used to compare predicted protection rate between study groups.

The criterion for evaluation of the primary endpoint 1 is: a similar percentage of subjects reaching the Bridge ELISA threshold that corresponds to 50% predicted vaccine efficacy after 2 doses of rF1V vaccine with CpG 1018® (CpG ODN 1018) adjuvant as compared to that after 3 doses of rF1V vaccine. The criterion for evaluation of the primary endpoint 2 is: 2-times increase of Bridge ELISA GMC point estimate after the second dose of rF1V vaccine with CpG 1018® (CpG ODN 1018) adjuvant compared to that after rF1V vaccine. The criteria for secondary objectives are GMC and seroconversion rate point estimates from rF1V vaccine with CpG 1018® (CpG ODN 1018) adjuvant to meet or exceed results from rF1V vaccine at relevant visits.

Safety data are being analyzed descriptively and are being based on the Safety Population. Summary statistics are being used to describe the incidence of all post-injection reactions, adverse events, including adverse events of special interest and serious adverse events, and deaths. Tables of adverse events are to include incidence, severity, seriousness, and relationship to the investigational vaccines.

Although the foregoing disclosure has been described in some detail by way of illustration and example for purposes of clarity and understanding, it will be apparent to those skilled in the art that certain changes and modifications may be practiced. Therefore, the examples should not be construed as limiting the scope of the disclosure, which is delineated by the appended claims.

SEQUENCES

```
>CpG
                                SEQ ID NO: 1
5'-TGACTGTGAA CGTTCGAGAT GA-3'

>rF1V (477 aa)
                                SEQ ID NO: 2
ADLTASTTATATLVEPARITLTYKEGAPITIMDNGNIDTELLVGT
LTLGGYKTGTTSTSVNFTDAAGDPMYLTFTSQDGNNHQFTTKVIG
KDSRDFDISPKVNGENLVGDDVVLATGSQDFFVRSIGSKGGKLAA
GKYTDAVTVTVSNQEFMIRAYEQNPQHFIEDLEKVRVEQLTGHGS
SVLEELVQLVKDKNIDISIKYDPRKDSEVFANRVITDDIELLKKI
LAYFLPEDTILKGGHYDNQLQNGIKRVKEFLESSPNTQWELRAFM
AVMHFSLTADRIDDDILKVIVDSMNHHGDARSKLREELAELTAEL
KIYSVIQAEINKHLSSSGTINIHDKSINLMDKNLYGYTDEEIFKA
SAEYKILEKMPQTTIQVDGSEKKIVSIKDFLGSENKRTGALGNLK
NSYSYNKDNNELSHFATTCSDKSRPLNDLVSQKTTQLSDITSRFN
SAIEALNRFIQKYDSVMQRLLDDTSGK

>rF1V-N-tag (521 aa)
                                SEQ ID NO: 3
MGHHHHHHHHHHSSGHIDDDDKHMKKISSVIAIALFGTIATANAA
DLTASTTATATLVEPARITLTYKEGAPITIMDNGNIDTELLVGTL
TLGGYKTGTTSTSVNFTDAAGDPMYLTFTSQDGNNHQFTTKVIGK
DSRDFDISPKVNGENLVGDDVVLATGSQDFFVRSIGSKGGKLAAG
```

-continued

SEQUENCES

```
KYTDAVTVTVSNQEFMIRAYEQNPQHFIEDLEKVRVEQLTGHGSS
VLEELVQLVKDKNIDISIKYDPRKDSEVFANRVITDDIELLKKIL
AYFLPEDTILKGGHYDNQLQNGIKRVKEFLESSPNTQWELRAFMA
VMHFSLTADRIDDDILKVIVDSMNHHGDARSKLREELAELTAELK
IYSVIQAEINKHLSSSGTINIHDKSINLMDKNLYGYTDEEIFKAS
AEYKILEKMPQTTIQVDGSEKKIVSIKDFLGSENKRTGALGNLKN
SYSYNKDNNELSHFATTCSDKSRPLNDLVSQKTTQLSDITSRFNS
AIEALNRFIQKYDSVMQRLLDDTSGK

>N-tag [HIS tag + 14 aa linker + enterokinase
cleavage site (DDD-K)]
                                SEQ ID NO: 4
MGHHHHHHHHHHSSGHIDDDDKH >F1sp
                                SEQ ID NO: 5
MKKISSVIAIALFGTIATANA >YpF1
                                SEQ ID NO: 6
ADLTASTTATATLVEPARITLTYKEGAPITIMDNGNIDTELLVGT
LTLGGYKTGTTSTSVNFTDAAGDPMYLTFTSQDGNNHQFTTKVIG
KDSRDFDISPKVNGENLVGDDVVLATGSQDFFVRSIGSKGGKLAA
GKYTDAVTVTVSNQ >Linker
EF >YpV
                                SEQ ID NO: 7
MIRAYEQNPQHFIEDLEKVRVEQLTGHGSSVLEELVQLVKDKNID
ISIKYDPRKDSEVFANRVITDDIELLKKILAYFLPEDTILKGGHY
DNQLQNGIKRVKEFLESSPNTQWELRAFMAVMHFSLTADRIDDDI
LKVIVDSMNHHGDARSKLREELAELTAELKIYSVIQAEINKHLSS
SGTINIHDKSINLMDKNLYGYTDEEIFKASAEYKILEKMPQTTIQ
VDGSEKKIVSIKDFLGSENKRTGALGNLKNSYSYNKDNNELSHFA
TTCSDKSRPLNDLVSQKTTQLSDITSRFNSAIEALNRFIQKYDSV
MQRLLDDTSGK >10mer Motif
                                SEQ ID NO: 8
5'-AACGTTCGAG-3'

>ODN 2006 aka ODN 7909
                                SEQ ID NO: 9
5'-TCGTCGTTTT GTCGTTTTGT CGTT-3'
```

We claim:

1. An immunogenic composition comprising:
   (i) an unmethylated cytidine-phospho-guanosine (CpG)-containing oligonucleotide comprising the sequence of 5'-TGACTGTGAA CGTTCGAGAT GA-3' (SEQ ID NO:1);
   (ii) at least one *Yersinia pestis* (*Y. pestis*) antigen; and
   (iii) an aluminum salt adjuvant,
   wherein the one dose of the immunogenic composition comprises the *Y. pestis* antigen in an amount of about 160 mcg, the oligonucleotide in an amount of about 3000 mcg, and the aluminum salt adjuvant in an amount of about 750 mcg $Al^{3+}$.

2. The composition of claim 1, wherein the *Y. pestis* antigen is a recombinant protein comprising an F1 antigen, a V antigen, both an F1 antigen and a V antigen, or an F1V fusion protein.

3. The composition of claim 1, wherein the *Y. pestis* antigen is a recombinant F1V (rF1V) fusion protein comprising an F1 antigen or fragment thereof and a V antigen or fragment thereof.

4. The composition of claim 3, wherein the F1 antigen comprises the amino acid sequence of SEQ ID NO:6 or an amino acid sequence having at least 90% sequence identity to SEQ ID NO:6, and the V antigen comprises the amino acid sequence of SEQ ID NO:7 or an amino acid sequence having at least 90% sequence identity to SEQ ID NO:7.

5. The composition of claim 3, wherein the rF1V fusion protein comprises the amino acid sequence of SEQ ID NO:2 or an amino acid sequence having at least 90% sequence identity to SEQ ID NO:2.

6. The composition of claim 3, wherein the rF1V fusion protein comprises the amino acid sequence of SEQ ID NO:2.

7. The composition of claim 3, wherein the rF1V fusion protein further comprises a signal peptide, the signal peptide comprising the amino acid sequence of SEQ ID NO: 5 or an amino acid sequence having at least 90% sequence identity to SEQ ID NO:5.

8. The composition of claim 1, wherein the oligonucleotide is 22, 23, 24, 25, 26, 27, 28, 29, 30, 31, 32, 33, 34, or 35 nucleotides in length.

9. The composition of claim 1, wherein the oligonucleotide is a single-stranded oligodeoxynucleotide.

10. The composition of claim 1, wherein the oligonucleotide comprises only phosphorothioate linkages, or a combination of one or more phosphodiester linkages and one or more phosphorothioate linkages.

11. The composition of claim 1, wherein the aluminum salt adjuvant is selected from the group consisting of amorphous aluminum hydroxyphosphate sulfate, aluminum hydroxide, aluminum phosphate, potassium aluminum sulfate, and combinations thereof.

12. A vial comprising an immunogenic composition comprising:
   (i) an unmethylated cytidine-phospho-guanosine (CpG)-containing oligonucleotide comprising the sequence of 5'-TGACTGTGAA CGTTCGAGAT GA-3' (SEQ ID NO:1);
   (ii) at least one *Yersinia pestis* (*Y. pestis*) antigen; and
   (iii) an aluminum salt adjuvant,
   wherein the one dose of the immunogenic composition comprises the *Y. pestis* antigen in an amount of about 160 mcg, the oligonucleotide in an amount of about 3000 mcg, and the aluminum salt adjuvant in an amount of about 750 mcg $Al^{3+}$.

13. A pre-filled syringe comprising an immunogenic composition comprising:
   (i) an unmethylated cytidine-phospho-guanosine (CpG)-containing oligonucleotide comprising the sequence of 5'-TGACTGTGAA CGTTCGAGAT GA-3' (SEQ ID NO:1);
   (ii) at least one *Yersinia pestis* (*Y. pestis*) antigen; and
   (iii) an aluminum salt adjuvant,
   wherein the one dose of the immunogenic composition comprises the *Y. pestis* antigen in an amount of about 160 mcg, the oligonucleotide in an amount of about 3000 mcg, and the aluminum salt adjuvant in an amount of about 750 mcg $Al^{3+}$.

14. A kit comprising:
   a) a first composition comprising an unmethylated cytidine-phospho-guanosine (CpG)-containing oligonucleotide comprising the sequence of 5'-TGACTGTGAA CGTTCGAGAT GA-3' (SEQ ID NO:1);
b) a second composition comprising at least one *Y. pestis* antigen and an aluminum salt adjuvant; and
c) instructions for combining the first composition and the second composition to prepare an immunogenic composition, wherein the one dose of the immunogenic composition comprises the *Y. pestis* antigen in an amount of about 160 mcg, the oligonucleotide in an amount of about 3000 mcg, and the aluminum salt adjuvant in an amount of about 750 mcg $Al^{3+}$.

15. A kit comprising:
a) a first composition comprising an unmethylated cytidine-phospho-guanosine (CpG)-containing oligonucleotide comprising the sequence of 5'-TGACTGTGAA CGTTCGAGAT GA-3' (SEQ ID NO:1);
b) a second composition comprising at least one *Y. pestis* antigen and an aluminum salt adjuvant; and
c) instructions for separate administration of the first and second compositions to a subject to stimulate an immune response against *Y. pestis* in the subject;
wherein the subject is to administered the *Y. pestis* antigen in an amount of about 160 mcg, the oligonucleotide in an amount of about 3000 mcg, and the aluminum salt adjuvant in an amount of about 750 mcg $Al^{3+}$.

* * * * *